US007179631B2

(12) United States Patent
Hahn et al.

(10) Patent No.: US 7,179,631 B2
(45) Date of Patent: Feb. 20, 2007

(54) HUMAN DEUBIQUITINATING PROTEASE GENE ON CHROMOSOME 7 AND ITS MURINE ORTHOLOG

(75) Inventors: Chang S. Hahn, Princeton, NJ (US); Hong Liu, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 515 days.

(21) Appl. No.: 10/379,981

(22) Filed: Mar. 5, 2003

(65) Prior Publication Data

US 2004/0001820 A1    Jan. 1, 2004

Related U.S. Application Data

(60) Provisional application No. 60/366,601, filed on Mar. 22, 2002.

(30) Foreign Application Priority Data

Aug. 9, 2002  (GB)  ................. 0218518.9

(51) Int. Cl.
*C12N 9/64* (2006.01)
*C07K 14/00* (2006.01)
*C12Q 1/37* (2006.01)
*C12P 21/06* (2006.01)
*C12N 15/00* (2006.01)
*C12N 1/20* (2006.01)
*C12N 5/00* (2006.01)
*C07H 21/04* (2006.01)

(52) U.S. Cl. .................. 435/226; 435/23; 435/69.1; 435/320.1; 435/252.3; 435/325; 530/350; 536/23.2; 536/23.5

(58) Field of Classification Search ............. 435/226, 435/23, 69.1, 320.1, 252.3, 325; 530/350; 536/23.2, 23.5
See application file for complete search history.

(56) References Cited

U.S. PATENT DOCUMENTS 6,287,858 B1    9/2001  D'Andrea

FOREIGN PATENT DOCUMENTS

| JP | 01128680 | 5/1989 |
|---|---|---|
| WO | WO 97/06247 | 2/1997 |
| WO | WO 00/01817 | 1/2000 |
| WO | WO 01/10903 | 2/2001 |
| WO | WO 01/23584 | 4/2001 |
| WO | WO 01/123589 | 4/2001 |

OTHER PUBLICATIONS

Quesada et al., Biochemical and Biophysical Research Communications 314:54-62, 2004.*
Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247, 1991.*
Isogai et al., GenBank accession No. BAB14232, Sep. 2000.*
Tanaka et al., FEBS 271:41-46, 1990.*
Baek Kwang-Hyun et al., DUB-2A, A New Member Of the DUB Subfamily Of Hematopoietic Deubiquitinating Enzymes, Blood (2001) 98 pp. 636-642.
Chung Chin Ha et al., Deubiquitinating Enzymes: Their Diversity And Emerging Roles, Biochemical And Biophysical Research Communications (1999) 266 pp. 633-640.
Jaster Robert et al., JAK2 Is Required For Induction Of The Murine DUB-1 Gene, Molecular And Cellular Biology (1997) pp. 3364-3372.
Johnston Steven C. et al., Crystal Structure Of A Deubiquitinating Enzyme (human UCH-L3) At 1.8 A resolution, The EMBO Journal (1997) 16 pp. 3787-3796.
Migone Thi-Sau et al., The Debiquitinating Enzyme DUB-2 Prolongs Cytokine-Induced Signal Tranducers And Activators Of Transcription Activation And Suppresses Apoptosis Following Cytokine Withdrawal, Blood (2001) 98 pp. 1935-1941.
Zhu Yuan et al., DUB-1, A Deubiquitinating Enzyme With Growth-Suppressing Activity, Proc. Nat'l. Acad. Sci. USA (1996) 93 pp. 3275-3279.
Zhu Yuan et al., DUB-2 Is A Member Of A Novel Family Of Cytokine-Inducible Deubiquitinating Enzymes, The Journal Of Biological Chemistry (1997) 272 pp. 51-57.
Zhu Yuan et al., The Murine DUB-1 Gene Is Specifically Induced by The Bc Subunit Of The Interleukin-3 Receptor, Molecular And Cellular Biology (1996) pp. 4808-4817.
Baker,R., Identification, Functional Characterization, and Chromosomal Localization of USP15, a Novel Human Ubiquitin-Specific Protease Related to the UNP Oncoprotein, and a Systematic Nomenclature for Human Ubiquitin-Specific Proteases, Genomics vol. 59, pp. 264-274 (1999).
Jans, D. et. al., Signals Mediating Nuclear Targeting and Their Regulation: Application in Drug Delivery, Medicinal Research Reviews, New York, NY, US vol. 18, No. 4 Jul. 1998 pp. 189-223, ISSN:0198-6325.

* cited by examiner

*Primary Examiner*—Delia M. Ramirez
(74) *Attorney, Agent, or Firm*—George S. Jones

(57) ABSTRACT

Human and murine analogs of DUBs, hematopoietic-specific, cytokine-inducible deubiquitinating proteases, clustered on chromosome 7 and and their respective regulatory regions are identified. The nucleotide or proteins encoded thereby may be used in assays to identify inhibitors of hDUB7, human deubiquitinating enzyme, or mDUB7, mouse deubiquitinating enzyme. The invention also includes transducing peptides comprising an NLS, nuclear localization signal, or transducing sequence of hDUB7 or mDUB7 linked to a cargo molecule, and methods of delivering a biologically active protein, therapeutically effective compound, antisense nucleotide, or test compound to a cell wherein a transducing peptide is added exogenously to a cell.

1 Claim, No Drawings

SEQUENCE LISTING

<160> NUMBER OF SEQ ID NOS: 12

<210> SEQ ID NO 1
<211> LENGTH: 19
<212> TYPE: PRT
<213> ORGANISM: Homo sapiens

<400> SEQUENCE: 1

```
Lys Ala Lys Lys His Lys Lys Ser Lys Lys Lys Lys Ser Lys Asp
1               5                   10                  15

Lys His Arg
```

<210> SEQ ID NO 2
<211> LENGTH: 16
<212> TYPE: PRT
<213> ORGANISM: Homo sapiens

<400> SEQUENCE: 2

His Arg His Lys Lys Lys Lys Lys Lys Lys Arg His Ser Arg Lys
1               5                   10                  15

<210> SEQ ID NO 3
<211> LENGTH: 17
<212> TYPE: PRT
<213> ORGANISM: Homo sapiens

<400> SEQUENCE: 3

Lys Lys His Lys Lys Ser Lys Lys Lys Lys Ser Lys Asp Lys His
1               5                   10                  15

Arg

<210> SEQ ID NO 4
<211> LENGTH: 16
<212> TYPE: PRT
<213> ORGANISM: Homo sapiens

<400> SEQUENCE: 4

His Arg His Arg Lys Lys Lys Lys Lys Lys Arg His Ser Arg Lys
1               5                   10                  15

<210> SEQ ID NO 5
<211> LENGTH: 23
<212> TYPE: DNA
<213> ORGANISM: Homo sapiens

<400> SEQUENCE: 5
ccacgacaga actgcacttg tag                                        23

<210> SEQ ID NO 6
<211> LENGTH: 19
<212> TYPE: DNA
<213> ORGANISM: Homo sapiens

<400> SEQUENCE: 6
ccgggacttt ccattttcg                                             19

<210> SEQ ID NO 7
<211> LENGTH: 31
<212> TYPE: DNA
<213> ORGANISM: Homo sapiens

<400> SEQUENCE: 7
caactgtaac ctctctgatc ggtttcacga a                               31

<210> SEQ ID NO 8
<211> LENGTH: 3951
<212> TYPE: DNA
<213> ORGANISM: Homo sapiens

<400> SEQUENCE: 8
atgaccatag ttgacaaagc ttctgaatct tcagacccat cagcctatca gaatcagcct    60
ggcagctccg aggcagtctc acctggagac atggatgcag ttctgccag ctggggtgct    120 gtgtcttcat tgaatgatgt gtcaaatcac acactttctt taggaccagt acctggtgct    180
gtagtttatt cgagttcatc tgtacctgat aaatcaaaac catcaccaca aaaggatcaa    240

-continued

```
gccctaggtg atggcatcgc tcctccacag aaagttcttt tcccatctga gaagatttgt      300
cttaagtggc aacaaactca tagagttgga gctgggctcc agaatttggg caatacctgt      360
tttgccaatg cagcactgca gtgtttaacc tacacaccac ctcttgccaa ttacatgcta      420
tcacatgaac actccaaaac atgtcatgca gaaggctttt gtatgatgtg tacaatgcaa      480
gcacatatta cccaggcact cagtaatcct ggggacgtta ttaaaccaat gtttgtcatc      540
aatgagatgc ggcgtatagc taggcacttc cgttttggaa accaagaaga tgcccatgaa      600
ttccttcaat acactgttga tgctatgcag aaagcatgct tgaatggcag caataaatta      660
gacagacaca cccaggccac cactcttgtt tgtcagatat ttggaggata cctaagatct      720
agagtcaaat gtttaaattg caagggcgtt tcagatactt ttgatccata tcttgatata      780
acattggaga taaaggctgc tcagagtgtc aacaaggcat ggagcagtt tgtgaagccg       840 gaacagcttg atggagaaaa ctcgtacaag tgcagcaagt gtaaaaagat ggttccagct      900
tcaaagaggt tcactatcca tagatcctct aatgttctta cactttctct gaaacgtttt      960
gcaaatttta ccggtggaaa aattgctaag gatgtgaaat accctgagta tcttgatatt     1020
cggccatata tgtctcaacc caacggagag ccaattgtct acgtcttgta tgcagtgctg     1080
gtccacactg gttttaattg ccatgctggc cattacttct gctacataaa agctagcaat     1140
ggcctctggt atcaaatgaa tgactccatt gtatctacca gtgatattag atcggtactc     1200
agccaacaag cctatgtgct ctttttatatc aggtcccatg atgtgaaaaa tggaggtgaa    1260
cttactcatc ccacccatag ccccggccag tcctctcccc gccccgtcat cagtcagcgg     1320
gttgtcacca acaaacaggc tgcgccaggc tttatcggac cacagcttcc ctctcacatg     1380
ataaagaatc cacctcactt aaatgggact ggaccattga agacacgcc aagcagttcc      1440 atgtcgagtc ctaacgggaa ttccagtgtc aacagggcta gtcctgttaa tgcttcagct     1500
tctgtccaaa actggtcagt taataggtcc tcagtgatcc cagaacatcc taagaaacaa     1560
aaaattacaa tcagtattca caacaagttg cctgttcgcc agtgtcagtc tcaacctaac     1620
cttcatagta attcttttgga gaaccctacc aagcccgttc cctcttctac cattaccaat    1680
tctgcagtac agtctaccct cgaacgcatct acgatgtcag tttctagtaa agtaacaaaa   1740
ccgatccccc gcagtgaatc ctgctcccag cccgtgatga atggcaaatc caagctgaac    1800
tccagcgtgc tggtgcccta tggcgccgag tcctctgagg actctgacga ggagtcaaag    1860
gggctgggca aggagaatgg gattggtacg attgtgagct cccactctcc cggccaagat    1920
gccgaagatg aggaggccac tccgcacgag cttcaagaac ccatgaccct aaacggtgct     1980
aatagtgcag acagcgacag tgacccgaaa gaaaacggcc tagcgcctga tggtgccagc     2040
tgccaaggcc agcctgccct gcactcagaa aatccctttg ctaaggcaaa cggtcttcct     2100
ggaaagttga tgcctgctcc tttgctgtct ctcccagaag acaaaatctt agagaccttc     2160
aggcttagca acaaactgaa aggctcgacg gatgaaatga gtgcacctgg agcagagagg     2220
ggccctcccg aggaccgcga cgccgagcct cagcctggca gccccgccgc cgaatccctg     2280
gaggagccag atgcggccgc cggcctcagc agcaccaaga aggctccgcc gccccgcgat     2340
cccggcaccc ccgctaccaa agaaggcgcc tgggaggcca tggccgtcgc ccccgaggag     2400
cctccgccca gcgccggcga ggacatcgtg ggggacacag caccccctga cctgtgtgat     2460
cccgggagct taacaggcga tgcgagcccc ttgtcccagg acgcaaaggg gatgatcgcg     2520
gagggcccgc gggactcggc gttggcggaa gccccggaag ggttgagtcc ggctccgcct     2580
```

-continued

```
gcgcggtcgg aggagccctg cgagcagcca ctccttgttc accccagcgg ggaccacgcc      2640
cgggacgctc aggacccatc ccagagcttg gcgcacccg aggccgcaga gcggccgcca       2700
gctcctgtgc tggacatggc cccggccggt cacccggaag gggacgctga gcctagcccc      2760
ggcgagaggg tcgaggacgc cgcggcgccg aaagccccag gcccttcccc agcgaaggag      2820
aaaatcggca gcctcagaaa ggtggaccga ggccactacc gcagccggag agagcgctcg      2880
tccagcgggg agcccgccag agagcagg agcaagactg agggccaccg tcaccggcgg        2940
cgccgcacct gcccccggga gcgcgaccgc caggaccgcc acgccccgga gcacccccc       3000 ggccacggcg acaggctcag ccctggcgag cgccgctctc tgggcaggtg cagtcaccac      3060
cactcccgac accggagcgg ggtggagctg gactgggtca gacaccacta caccgagggc      3120
gagcgtggct ggggccggga gaagttctac cccgacaggc cgcgctggga caggtgccgg      3180
tactaccatg acaggtacgc cctgtacgct gcccgggact ggaagccctt ccacggcggc      3240
cgcgagcacg agcgggccgg gctgcacgag cggccgcaca aggaccacaa ccggggccgt      3300
aggggctgcg agccggcccg ggagagggag cggcaccgcc ccagcagccc ccgcgcaggc      3360 gcgcccacg ccctcgcccc gcaccccgac cgcttctccc acgacagaac tgcacttgta       3420
gccggagaca actgtaacct ctctgatcgg tttcacgaac acgaaaatgg aaagtcccgg      3480
aaacggagac acgacagtgt ggagaacagt gacagtcatg ttgaaaagaa agcccggagg      3540
agcgaacaga aggatcctct agaagagcct aaagcaaaga agcacaaaaa atcaaagaag      3600
aaaaagaaat ccaaagacaa acaccgagac cgcgactcca ggcatcagca ggactcagac      3660
ctctcagcag cgtgctctga cgctgacctc cacagacaca aaaaaaagaa gaagaaaaag      3720
aagagacatt caagaaaatc agaggacttt gttaaagatt cagaactgca cttacccagg      3780
gtcaccagct tggagactgt cgcccagttc cggagagccc agggtggctt tcctctctct      3840
ggtggcccgc tctgcgaagg cgtcggacct ttccgtgaga aaacgaaaca cttacggatg      3900
gaaagcaggg atgacaggtg tcgtctcttt gagtatggcc agggtgattg a               3951
```

<210> SEQ ID NO 9
<211> LENGTH: 1316
<212> TYPE: PRT
<213> ORGANISM: Homo sapiens

<400> SEQUENCE: 9

```
Met Thr Ile Val Asp Lys Ala Ser Glu Ser Asp Pro Ser Ala Tyr
1               5                   10                  15

Gln Asn Gln Pro Gly Ser Ser Glu Ala Val Ser Pro Gly Asp Met Asp
                20                  25                  30

Ala Gly Ser Ala Ser Trp Gly Ala Val Ser Ser Leu Asn Asp Val Ser
            35                  40                  45

Asn His Thr Leu Ser Leu Gly Pro Val Pro Gly Ala Val Val Tyr Ser
        50                  55                  60

Ser Ser Ser Val Pro Asp Lys Ser Lys Pro Ser Pro Gln Lys Asp Gln
    65                  70                  75                  80

Ala Leu Gly Asp Gly Ile Ala Pro Pro Gln Lys Val Leu Phe Pro Ser
                85                  90                  95

Glu Lys Ile Cys Leu Lys Trp Gln Gln Thr His Arg Val Gly Ala Gly
                100                 105                 110

Leu Gln Asn Leu Gly Asn Thr Cys Phe Ala Asn Ala Ala Leu Gln Cys
            115                 120                 125

Leu Thr Tyr Thr Pro Pro Leu Ala Asn Tyr Met Leu Ser His Glu His
```

-continued

```
            130                 135                 140
Ser Lys Thr Cys His Ala Glu Gly Phe Cys Met Met Cys Thr Met Gln
145                 150                 155                 160

Ala His Ile Thr Gln Ala Leu Ser Asn Pro Gly Asp Val Ile Lys Pro
                165                 170                 175

Met Phe Val Ile Asn Glu Met Arg Arg Ile Ala Arg His Phe Arg Phe
                180                 185                 190

Gly Asn Gln Glu Asp Ala His Glu Phe Leu Gln Tyr Thr Val Asp Ala
                195                 200                 205

Met Gln Lys Ala Cys Leu Asn Gly Ser Asn Lys Leu Asp Arg His Thr
210                 215                 220

Gln Ala Thr Thr Leu Val Cys Gln Ile Phe Gly Gly Tyr Leu Arg Ser
225                 230                 235                 240

Arg Val Lys Cys Leu Asn Cys Lys Gly Val Ser Asp Thr Phe Asp Pro
                245                 250                 255

Tyr Leu Asp Ile Thr Leu Glu Ile Lys Ala Ala Gln Ser Val Asn Lys
                260                 265                 270

Ala Leu Glu Gln Phe Val Lys Pro Glu Gln Leu Asp Gly Glu Asn Ser
                275                 280                 285

Tyr Lys Cys Ser Lys Cys Lys Lys Met Val Pro Ala Ser Lys Arg Phe
290                 295                 300

Thr Ile His Arg Ser Ser Asn Val Leu Thr Leu Ser Leu Lys Arg Phe
305                 310                 315                 320

Ala Asn Phe Thr Gly Gly Lys Ile Ala Lys Asp Val Lys Tyr Pro Glu
                325                 330                 335

Tyr Leu Asp Ile Arg Pro Tyr Met Ser Gln Pro Asn Gly Glu Pro Ile
                340                 345                 350

Val Tyr Val Leu Tyr Ala Val Leu Val His Thr Gly Phe Asn Cys His
                355                 360                 365

Ala Gly His Tyr Phe Cys Tyr Ile Lys Ala Ser Asn Gly Leu Trp Tyr
                370                 375                 380

Gln Met Asn Asp Ser Ile Val Ser Thr Ser Asp Ile Arg Ser Val Leu
385                 390                 395                 400

Ser Gln Gln Ala Tyr Val Leu Phe Tyr Ile Arg Ser His Asp Val Lys
                405                 410                 415

Asn Gly Gly Glu Leu Thr His Pro Thr His Ser Pro Gly Gln Ser Ser
                420                 425                 430

Pro Arg Pro Val Ile Ser Gln Arg Val Val Thr Asn Lys Gln Ala Ala
                435                 440                 445

Pro Gly Phe Ile Gly Pro Gln Leu Pro Ser His Met Ile Lys Asn Pro
                450                 455                 460

Pro His Leu Asn Gly Thr Gly Pro Leu Lys Asp Thr Pro Ser Ser Ser
465                 470                 475                 480

Met Ser Ser Pro Asn Gly Asn Ser Ser Val Asn Arg Ala Ser Pro Val
                485                 490                 495

Asn Ala Ser Ala Ser Val Gln Asn Trp Ser Val Asn Arg Ser Ser Val
                500                 505                 510

Ile Pro Glu His Pro Lys Lys Gln Lys Ile Thr Ile Ser Ile His Asn
                515                 520                 525

Lys Leu Pro Val Arg Gln Cys Gln Ser Gln Pro Asn Leu His Ser Asn
                530                 535                 540

Ser Leu Glu Asn Pro Thr Lys Pro Val Pro Ser Ser Thr Ile Thr Asn
545                 550                 555                 560
```

```
Ser Ala Val Gln Ser Thr Ser Asn Ala Ser Thr Met Ser Val Ser Ser
            565                 570                 575

Lys Val Thr Lys Pro Ile Pro Arg Ser Glu Cys Ser Gln Pro Val
            580                 585                 590

Met Asn Gly Lys Ser Lys Leu Asn Ser Ser Val Leu Val Pro Tyr Gly
            595                 600                 605

Ala Glu Ser Ser Glu Asp Ser Asp Glu Ser Lys Gly Leu Gly Lys
    610                 615                 620

Glu Asn Gly Ile Gly Thr Ile Val Ser Ser His Ser Pro Gly Gln Asp
625                 630                 635                 640

Ala Glu Asp Glu Glu Ala Thr Pro His Glu Leu Gln Glu Pro Met Thr
                    645                 650                 655

Leu Asn Gly Ala Asn Ser Ala Asp Ser Asp Ser Asp Pro Lys Glu Asn
                660                 665                 670

Gly Leu Ala Pro Asp Gly Ala Ser Cys Gln Gly Gln Pro Ala Leu His
            675                 680                 685

Ser Glu Asn Pro Phe Ala Lys Ala Asn Gly Leu Pro Gly Lys Leu Met
    690                 695                 700

Pro Ala Pro Leu Leu Ser Leu Pro Glu Asp Lys Ile Leu Glu Thr Phe
705                 710                 715                 720

Arg Leu Ser Asn Lys Leu Lys Gly Ser Thr Asp Glu Met Ser Ala Pro
                725                 730                 735

Gly Ala Glu Arg Gly Pro Pro Glu Asp Arg Asp Ala Glu Pro Gln Pro
                740                 745                 750

Gly Ser Pro Ala Ala Glu Ser Leu Glu Glu Pro Asp Ala Ala Ala Gly
            755                 760                 765

Leu Ser Ser Thr Lys Lys Ala Pro Pro Arg Asp Pro Gly Thr Pro
    770                 775                 780

Ala Thr Lys Glu Gly Ala Trp Glu Ala Met Ala Val Ala Pro Glu Glu
785                 790                 795                 800

Pro Pro Pro Ser Ala Gly Glu Asp Ile Val Gly Asp Thr Ala Pro Pro
                805                 810                 815

Asp Leu Cys Asp Pro Gly Ser Leu Thr Gly Asp Ala Ser Pro Leu Ser
                820                 825                 830

Gln Asp Ala Lys Gly Met Ile Ala Glu Gly Pro Arg Asp Ser Ala Leu
            835                 840                 845

Ala Glu Ala Pro Glu Gly Leu Ser Pro Ala Pro Pro Ala Arg Ser Glu
    850                 855                 860

Glu Pro Cys Glu Gln Pro Leu Leu Val His Pro Ser Gly Asp His Ala
865                 870                 875                 880

Arg Asp Ala Gln Asp Pro Ser Gln Ser Leu Gly Ala Pro Glu Ala Ala
                885                 890                 895

Glu Arg Pro Pro Ala Pro Val Leu Asp Met Ala Pro Ala Gly His Pro
            900                 905                 910

Glu Gly Asp Ala Glu Pro Ser Pro Gly Glu Arg Val Glu Asp Ala Ala
    915                 920                 925

Ala Pro Lys Ala Pro Gly Pro Ser Pro Ala Lys Glu Lys Ile Gly Ser
    930                 935                 940

Leu Arg Lys Val Asp Arg Gly His Tyr Arg Ser Arg Glu Arg Ser
945                 950                 955                 960

Ser Ser Gly Glu Pro Ala Arg Glu Ser Arg Ser Lys Thr Glu Gly His
            965                 970                 975
```

```
Arg His Arg Arg Arg Thr Cys Pro Arg Glu Arg Asp Arg Gln Asp
            980                 985                 990

Arg His Ala Pro Glu His His Pro  Gly His Gly Asp Arg  Leu Ser Pro
            995                 1000                1005

Gly Glu  Arg Arg Ser Leu Gly  Arg Cys Ser His  His  His Ser Arg
            1010                1015                1020

His Arg  Ser Gly Val Glu Leu  Asp Trp Val Arg His  His Tyr Thr
            1025                1030                1035

Glu Gly  Glu Arg Gly Trp Gly  Arg Glu Lys Phe Tyr  Pro Asp Arg
            1040                1045                1050

Pro Arg  Trp Asp Arg Cys Arg  Tyr Tyr His Asp Arg  Tyr Ala Leu
            1055                1060                1065

Tyr Ala  Ala Arg Asp Trp Lys  Pro Phe His Gly Gly  Arg Glu His
            1070                1075                1080

Glu Arg  Ala Gly Leu His Glu  Arg Pro His Lys Asp  His Asn Arg
            1085                1090                1095

Gly Arg  Arg Gly Cys Glu Pro  Ala Arg Glu Arg Glu  Arg His Arg
            1100                1105                1110

Pro Ser  Ser Pro Arg Ala Gly  Ala Pro His Ala Leu  Ala Pro His
            1115                1120                1125

Pro Asp  Arg Phe Ser His Asp  Arg Thr Ala Leu Val  Ala Gly Asp
            1130                1135                1140

Asn Cys  Asn Leu Ser Asp Arg  Phe His Glu His Glu  Asn Gly Lys
            1145                1150                1155

Ser Arg  Lys Arg Arg His Asp  Ser Val Glu Asn Ser  Asp Ser His
            1160                1165                1170

Val Glu  Lys Lys Ala Arg Arg  Ser Glu Gln Lys Asp  Pro Leu Glu
            1175                1180                1185

Glu Pro  Lys Ala Lys Lys His  Lys Lys Ser Lys Lys  Lys Lys Lys
            1190                1195                1200

Ser Lys  Asp Lys His Arg Asp  Arg Asp Ser Arg His  Gln Gln Asp
            1205                1210                1215

Ser Asp  Leu Ser Ala Ala Cys  Ser Asp Ala Asp Leu  His Arg His
            1220                1225                1230

Lys Lys  Lys Lys Lys Lys Lys  Lys Arg His Ser Arg  Lys Ser Glu
            1235                1240                1245

Asp Phe  Val Lys Asp Ser Glu  Leu His Leu Pro Arg  Val Thr Ser
            1250                1255                1260

Leu Glu  Thr Val Ala Gln Phe  Arg Arg Ala Gln Gly  Gly Phe Pro
            1265                1270                1275

Leu Ser  Gly Gly Pro Pro Leu  Glu Gly Val Gly Pro  Phe Arg Glu
            1280                1285                1290

Lys Thr  Lys His Leu Arg Met  Glu Ser Arg Asp Asp  Arg Cys Arg
            1295                1300                1305

Leu Phe  Glu Tyr Gly Gln Gly  Asp
            1310                1315

<210> SEQ ID NO 10
<211> LENGTH: 2001
<212> TYPE: DNA
<213> ORGANISM: Homo sapiens

<400> SEQUENCE: 10
gtaaagtcta aactgagaag tggaagtgtg aactggctgg aggtggaagg ttggaaaaga       60
```

-continued

| | |
|---|---|
| gtcggagaaa agaacagcat gtgcagagcc cagagacagc agggacaaaa gaaaaaaaaa | 120 |
| caagacttca gcatggtggg aacgtgacgg agagggtgtt tggcgaggtt attaggtcag | 180 |
| acaatgtgaa gtccagacat taagatgttg tgctgtgggc agttgggcca ctcctgaaag | 240 |
| gtgttctttc ttcctttcct tttctttctt tcttttcttg aggcagagtc tctctatgtc | 300 |
| agtctggagt gcagtggcat gatctcggct cactgcaatc tctgccttcc aggttcaagc | 360 |
| aattttcctt gcctcagcct cccaagtagc tgggaataca ggcgtgcgcc accatgcctg | 420 |
| gttaattttt ttattttag tagagatggg gtttccccat gttggccagg ctggtctcga | 480 |
| actcctggac tcaagtgatc cacccacttt ggcctcccaa agtgctggga ttacaggggt | 540 |
| gtgagccact gcgccccgcc cggccttttt tttttttttt tttgagactt aatcttgctc | 600 |
| tgtcaccaag gctggatatc agtggcacgg ttttggctct ctgcaacttc tgtctcccag | 660 |
| gttcaagcga ttttcctgac tcagcctccc aagtagttga gattacaggt acgtgccacc | 720 |
| acgcccggct aattttgta tttttagtag agatgaggtt tcactatgtt ggccagactg | 780 |
| gtctcaaacg cctgacctca ggtgattcac ctgcctcggc ctcccaaaat gctgggatta | 840 |
| caggtgtgca ccaccatgcc tgggtaattt ttgttttcg tagagacagg gtctcaccat | 900 |
| gttggccagg ctggtctcaa actcctgacc tcaagcgatc tgcccacctt ggcctcccaa | 960 |
| ggtgctgcaa ttataggcat gagccaccgc gcccggcctc ctgaaaggtt ttctacatag | 1020 |
| gagtggcatg tctagatgtg gctactgttg ggcgatttta gaaatatccc taaaagcctt | 1080 |
| ctgttgacag ggtggcataa ccagaaggaa gcctggctgg gaacgctgga cctggctctc | 1140 |
| agtcccagtt gctgactggt tgcttcattt tataggccct ggggattctg tctgatctct | 1200 |
| catacgttct ttataaaaat taagttaatg tatgtccagc agttgatgca atgcccagta | 1260 |
| catagaaaat gctcaattag tggtagccct aatattttaa aataggactc agaaagaaaa | 1320 |
| ttataatcaa gtcctttcat aacagatatt tgtgtttgag tttgatatca gtaatggctt | 1380 |
| acgggtttta tttaaaaagt catacattcc atataaatga gcctcttcag aaaaatggtt | 1440 |
| ttaaaggtga gatctctata attataattt taaaaaatat aatgtatttc acttggtgcc | 1500 |
| atttgcactt taagcacaaa attaagtcta gattttttct gtgtagttga tgcttttctc | 1560 |
| tgaggaatta tactcaaatt gaagatgtag tcaaatgtat tactgtgtat aattttcta | 1620 |
| gttttaagca gtatagaagg aaaatatagg tacttagtaa ataaacagaa ctgagaattg | 1680 |
| aaatgtccaa ttataaactg aaatgccaga cttttagggg gcatgaaatg aaaatgagaa | 1740 |
| gttcttttaa tcaaatactt cactgaagat tttaaaataa agattgttga cattcagatt | 1800 |
| atcatgatgc taaatgtccc aaggggatta ttacagaaat gttagaaagt actattgttt | 1860 |
| ttatatttga gtgatgtgtt tgaaaatcac tttaaaatgc tggaatgat cttccaagat | 1920 |
| ctaacggtag ggtaaggaga ttgcttttct cacctgatga aacaaataca tacttttcat | 1980 |
| cttttgcaga gttgaacaat g | 2001 |

<210> SEQ ID NO 11
<211> LENGTH: 3981
<212> TYPE: DNA
<213> ORGANISM: Mus musculus

<400> SEQUENCE: 11

| | |
|---|---|
| atgaccatag ttgacaaaac tgaaccttca gacccatcaa cctgtcagaa ccagcctggc | 60 |
| agttgtgagg cggtctcacc tgaagacatg gacacaggct ctgccagctg ggcgctgtg | 120 |
| tcttcaataa gtgatgtctc aagtcacaca cttccattag ggccagtgcc tggtgctgta | 180 |

-continued

```
gtttattcta actcgtctgt acctgaaaaa tcaaagccat caccaccaaa ggatcaagtc      240
ctaggtgatg gcattgctcc tcctcaaaag gtcctgtttc catctgaaaa gatttgtctt      300
aagtggcaac aaagtcatcg agttggcgct gggctccaga atttgggcaa cacctgtttt      360
gccaatgccg cattgcagtg tctgacttac acgccacccc tcgccaatta catgttatcc      420
catgaacact ccaagacatg ccacgcagaa ggattttgta tgatgtgcac gatgcagaca      480
cacattaccc aggcacttag caaccctggg gatgttatca agccgatgtt cgtcatcaat      540
gaaatgcggc gtatagctag acacttccgt tttggaaacc aagaagatgc ccatgaattt      600
cttcagtaca cggtcgatgc catgcagaaa gcatgtttaa atggcagcaa taaattagac      660
agacacaccc aggccaccac cctggtctgc cagatatttg gaggctacct aagatcccga      720
gttaaatgtt taaattgcaa gggtgtttca gatacctttg atccatatct ggacataacg      780
ttggagatta aggctgcaca gagtgttacc aaggcgttag agcagtttgt gaagccagaa      840
caactggatg gagaaaactc ctacaagtgc agcaagtgca aaaaaatggt tccagcttca      900
aagagattca caatccatag gtcctctaat gttcttacca tctcactgaa gcgctttgcc      960
aacttcaccg gtggaaagat tgctaaggat gtgaaatatc ctgagtacct tgatatccgg     1020
ccctatatgt ctcagcccaa tggagagcca attatttatg ttttgtatgc gtgctggtg      1080 cacactggtt ttaattgtca tgctggccac tactttgct acatcaaggc tagcaatggc      1140
ctctggtatc agatgaatga ctccatcgtg tccaccagtg atatcagagc agtgcttaac     1200
cagcaagctt acgtgctctt ttatatcagg tcccatgatg tgaaaaatgg aggggagtct     1260
gctcatcctg cccatagccc cggccaatcc tctccccgcc caggagtcag tcagcgggta     1320
gtcaacaaca gcaggtggc tccagggttt attggacccc agctgccttc ccatgtgatg     1380
aagaacacgc cacacttgaa tggcaccacg ccagtgaaag acacaccaag tagttctgtg     1440
tcaagcccta acggaaacac cagcgtcaat agggccagtc ctgctactgc ttcgacttct     1500
gtgcagaact ggtctgttac cagaccctca gttattccag atcaccccaa gaaacaaaaa     1560
atcaccatca gtattcacaa caagttgcct gctcgccagg gtcaggcacc actgaataac     1620
agcctccatg gcccttgtct ggaggctcct agtaaggcgg cacctcctc caccatcact     1680 aaccttctg caatacagtc tacctcgaac gtacccacaa cgtcgacttc ccccagtgag     1740
gcctgtccca gcccatggt gaacggcaag gctaaagtgg gcgccagtgt gcttgtcccc     1800 tatgggccg agtcctcaga agagtctgat gaggagtcga agggcctggc caaggagaac     1860
ggtgtggaca tgatggccgg cactcactcc gataggccag aagctgctgc agatgacggt     1920
gctgaggctt cctcccatga gcttcaagaa cccgtcctgc taaatggtgc taatagcgca     1980
gacagtgact cacaagagaa cagcctggca tttgacagtg ccagctgcca ggtccagccc     2040
gagctacaca cagaaaacct cttttccaaa cttaatggtc ttcctggaaa ggtgacgcct     2100
gctcctttgc agtctgttcc tgaagacaga atccttgaga ccttcaagct taccaaccag     2160
gcaaagggtc cagcgggtga agagagttgg actacgacag ggggaagctc tccaaaggac     2220
cctgtttcac agctggagcc catcagtgat gagcccagtc ccttgagat accggaggct      2280 gtcaccaatg ggagcacaca gaccccttcc accacatcac ccctggagcc caccatcagc     2340
tgtaccaaag aagactcgtc cgttgttgtc tcagctgaac ctgtggaggg tttgccttcc     2400
gtccctgctc tttgtaacag cactggtact atcttggggg ataccccagt gcccgaattg     2460
tgtgaccctg gagacttgac tgccaacccg agccagccaa ccgaagcagt gaaaggtgat     2520
```

-continued

```
acagctgaga aggctcagga ctctgccatg gctgaagtgg tggagaggct gagccctgct    2580
ccctcagtac tcacaggtga cgggtgtgag cagaaactct tactttacct cagcgcagag    2640
gggtcagagg agacagaaga ctcttccaga agctcggcgg tctctgctga cacgatgccc    2700
cctaagcctg acaggaccac caccagctcc tgtgaagggg ctgccgagca ggctgctggg    2760
gacagaggcg atggaggcca tgtgggaccc aaagctcagg agccttcccc agccaaggaa    2820
aagatgagca gcctccggaa agtggaccga ggacactatc ggagccggag agagcgctcc    2880
tccagtgggg agcacgtgag ggacagcagg ccccggccgg aggaccatca ccataagaag    2940
cggcactgct acagccgaga gcggcccaag caggaccgac ccctactaa ttcatactgc     3000 aatgggggcc agcacttggg ccacggggac agagccagcc ctgagcgccg ctccctgagc    3060
aggtatagtc accaccactc acggattagg agtggcctgg agcaggactg gagccggtac    3120
caccatttgg aaaatgagca tgcttgggtc agggagagat tctaccagga caagctgcgg    3180
tgggacaagt gcaggtatta ccacgacagg tacgcccc tatacacggc ccgggacgcc       3240
cgagaatggc ggcctctgca tggtcgtgag catgaccgcc ttgtccagtc tggacggcca    3300
tacaaggaca gctactgggg ccgcaagggc tgggagctgc aatcccgggg gaaggaacgg    3360
ccccacttca acagcccccg agaggcccct agccttgctg tgcccctcga gagacatctc    3420
caagagaagg ctgcgctgag tgtgcaggac agcagccaca gtctccctga gcgctttcat    3480
gaacacaaaa gtgtcaagtc gaggaagcgg aggtatgaga ctctagaaaa taatgatggc    3540
cgtctagaaa agaaagtcca caaaagcctg gagaaggaca cgctagagga gccaagggtg    3600
aagaagcaca aaaagtctaa aaagaaaaag aagtccaaag ataaacaccg ggatcgagaa    3660
agcaggcacc agcaggagtc tgatttttca ggagcatact ctgatgctga cctccataga    3720
caccggaaga aaagaagaa aaagaaaagg cattccagga agtcggagga ctttataaag      3780
gatgttgaga tgcgtttacc gaagctctcc agctacgagg ccggcggcca tttccggaga    3840
acagagggca gctttctcct ggctgatggt ctgcctgtgg aagacagcgg cccttccgg     3900 gagaaaacga agcatttaag gatggaaagc cggcctgaca gatgccgtct gtcggagtat    3960
ggccaggatt caacattttg a                                              3981
```

<210> SEQ ID NO 12
<211> LENGTH: 1326
<212> TYPE: PRT
<213> ORGANISM: Mus musculus

<400> SEQUENCE: 12

```
Met Thr Ile Val Asp Lys Thr Glu Pro Ser Asp Pro Ser Thr Cys Gln
1               5                   10                  15

Asn Gln Pro Gly Ser Cys Glu Ala Val Ser Pro Glu Asp Met Asp Thr
            20                  25                  30

Gly Ser Ala Ser Trp Gly Ala Val Ser Ile Ser Asp Val Ser Ser
        35                  40                  45

His Thr Leu Pro Leu Gly Pro Val Gly Ala Val Val Tyr Ser Asn
    50                  55                  60

Ser Ser Val Pro Glu Lys Ser Lys Pro Ser Pro Lys Asp Gln Val
65                  70                  75                  80

Leu Gly Asp Gly Ile Ala Pro Pro Gln Lys Val Leu Phe Pro Ser Glu
                85                  90                  95

Lys Ile Cys Leu Lys Trp Gln Gln Ser His Arg Val Gly Ala Gly Leu
            100                 105                 110
```

```
Gln Asn Leu Gly Asn Thr Cys Phe Ala Asn Ala Ala Leu Gln Cys Leu
        115                 120                 125

Thr Tyr Thr Pro Pro Leu Ala Asn Tyr Met Leu Ser His Glu His Ser
130                 135                 140

Lys Thr Cys His Ala Glu Gly Phe Cys Met Met Cys Thr Met Gln Thr
145                 150                 155                 160

His Ile Thr Gln Ala Leu Ser Asn Pro Gly Asp Val Ile Lys Pro Met
                165                 170                 175

Phe Val Ile Asn Glu Met Arg Arg Ile Ala Arg His Phe Arg Phe Gly
                180                 185                 190

Asn Gln Glu Asp Ala His Glu Phe Leu Gln Tyr Thr Val Asp Ala Met
                195                 200                 205

Gln Lys Ala Cys Leu Asn Gly Ser Asn Lys Leu Asp Arg His Thr Gln
        210                 215                 220

Ala Thr Thr Leu Val Cys Gln Ile Phe Gly Gly Tyr Leu Arg Ser Arg
225                 230                 235                 240

Val Lys Cys Leu Asn Cys Lys Gly Val Ser Asp Thr Phe Asp Pro Tyr
                245                 250                 255

Leu Asp Ile Thr Leu Glu Ile Lys Ala Ala Gln Ser Val Thr Lys Ala
                260                 265                 270

Leu Glu Gln Phe Val Lys Pro Glu Gln Leu Asp Gly Glu Asn Ser Tyr
        275                 280                 285

Lys Cys Ser Lys Cys Lys Lys Met Val Pro Ala Ser Lys Arg Phe Thr
        290                 295                 300

Ile His Arg Ser Ser Asn Val Leu Thr Ile Ser Leu Lys Arg Phe Ala
305                 310                 315                 320

Asn Phe Thr Gly Gly Lys Ile Ala Lys Asp Val Lys Tyr Pro Glu Tyr
                325                 330                 335

Leu Asp Ile Arg Pro Tyr Met Ser Gln Pro Asn Gly Glu Pro Ile Ile
                340                 345                 350

Tyr Val Leu Tyr Ala Val Leu Val His Thr Gly Phe Asn Cys His Ala
        355                 360                 365

Gly His Tyr Phe Cys Tyr Ile Lys Ala Ser Asn Gly Leu Trp Tyr Gln
        370                 375                 380

Met Asn Asp Ser Ile Val Ser Thr Ser Asp Ile Arg Ala Val Leu Asn
385                 390                 395                 400

Gln Gln Ala Tyr Val Leu Phe Tyr Ile Arg Ser His Asp Val Lys Asn
                405                 410                 415

Gly Gly Glu Ser Ala His Pro Ala His Ser Pro Gly Gln Ser Ser Pro
                420                 425                 430

Arg Pro Gly Val Ser Gln Arg Val Val Asn Asn Lys Gln Val Ala Pro
                435                 440                 445

Gly Phe Ile Gly Pro Gln Leu Pro Ser His Val Met Lys Asn Thr Pro
        450                 455                 460

His Leu Asn Gly Thr Thr Pro Val Lys Asp Thr Pro Ser Ser Ser Val
465                 470                 475                 480

Ser Ser Pro Asn Gly Asn Thr Ser Val Asn Arg Ala Ser Pro Ala Thr
                485                 490                 495

Ala Ser Thr Ser Val Gln Asn Trp Ser Val Thr Arg Pro Ser Val Ile
                500                 505                 510

Pro Asp His Pro Lys Lys Gln Lys Ile Thr Ile Ser Ile His Asn Lys
                515                 520                 525

Leu Pro Ala Arg Gln Gly Gln Ala Pro Leu Asn Asn Ser Leu His Gly
```

-continued

```
            530                 535                 540
Pro Cys Leu Glu Ala Pro Ser Lys Ala Ala Pro Ser Ser Thr Ile Thr
545                 550                 555                 560

Asn Pro Ser Ala Ile Gln Ser Thr Ser Asn Val Pro Thr Thr Ser Thr
                565                 570                 575

Ser Pro Ser Glu Ala Cys Pro Lys Pro Met Val Asn Gly Lys Ala Lys
                580                 585                 590

Val Gly Ala Ser Val Leu Val Pro Tyr Gly Ala Glu Ser Ser Glu Glu
                595                 600                 605

Ser Asp Glu Glu Ser Lys Gly Leu Ala Lys Glu Asn Gly Val Asp Met
610                 615                 620

Met Ala Gly Thr His Ser Asp Arg Pro Glu Ala Ala Asp Asp Gly
625                 630                 635                 640

Ala Glu Ala Ser Ser His Glu Leu Gln Glu Pro Val Leu Leu Asn Gly
                645                 650                 655

Ala Asn Ser Ala Asp Ser Asp Ser Gln Glu Asn Ser Leu Ala Phe Asp
                660                 665                 670

Ser Ala Ser Cys Gln Val Gln Pro Glu Leu His Thr Glu Asn Leu Phe
                675                 680                 685

Ser Lys Leu Asn Gly Leu Pro Gly Lys Val Thr Pro Ala Pro Leu Gln
                690                 695                 700

Ser Val Pro Glu Asp Arg Ile Leu Glu Thr Phe Lys Leu Thr Asn Gln
705                 710                 715                 720

Ala Lys Gly Pro Ala Gly Glu Glu Ser Trp Thr Thr Gly Gly Ser
                725                 730                 735

Ser Pro Lys Asp Pro Val Ser Gln Leu Glu Pro Ile Ser Asp Glu Pro
                740                 745                 750

Ser Pro Leu Glu Ile Pro Glu Ala Val Thr Asn Gly Ser Thr Gln Thr
                755                 760                 765

Pro Ser Thr Thr Ser Pro Leu Glu Pro Thr Ile Ser Cys Thr Lys Glu
                770                 775                 780

Asp Ser Ser Val Val Ser Ala Glu Pro Val Glu Gly Leu Pro Ser
785                 790                 795                 800

Val Pro Ala Leu Cys Asn Ser Thr Gly Thr Ile Leu Gly Asp Thr Pro
                805                 810                 815

Val Pro Glu Leu Cys Asp Pro Gly Asp Leu Thr Ala Asn Pro Ser Gln
                820                 825                 830

Pro Thr Glu Ala Val Lys Gly Asp Thr Ala Glu Lys Ala Gln Asp Ser
                835                 840                 845

Ala Met Ala Glu Val Val Glu Arg Leu Ser Pro Ala Pro Ser Val Leu
850                 855                 860

Thr Gly Asp Gly Cys Glu Gln Lys Leu Leu Leu Tyr Leu Ser Ala Glu
865                 870                 875                 880

Gly Ser Glu Glu Thr Glu Asp Ser Ser Arg Ser Ser Ala Val Ser Ala
                885                 890                 895

Asp Thr Met Pro Pro Lys Pro Asp Arg Thr Thr Thr Ser Ser Cys Glu
                900                 905                 910

Gly Ala Ala Glu Gln Ala Ala Gly Asp Arg Gly Asp Gly Gly His Val
                915                 920                 925

Gly Pro Lys Ala Gln Glu Pro Ser Pro Ala Lys Glu Lys Met Ser Ser
                930                 935                 940

Leu Arg Lys Val Asp Arg Gly His Tyr Arg Ser Arg Glu Arg Ser
945                 950                 955                 960
```

-continued

Ser Ser Gly Glu His Val Arg Asp Ser Arg Pro Arg Pro Glu Asp His
              965                 970                 975

His His Lys Lys Arg His Cys Tyr Ser Arg Glu Arg Pro Lys Gln Asp
        980                 985                 990

Arg His Pro Thr Asn Ser Tyr Cys Asn Gly Gly Gln His Leu Gly His
      995                 1000                1005

Gly Asp Arg Ala Ser Pro Glu Arg Arg Ser Leu Ser Arg Tyr Ser
    1010                1015                1020

His His His Ser Arg Ile Arg Ser Gly Leu Glu Gln Asp Trp Ser
    1025                1030                1035

Arg Tyr His His Leu Glu Asn Glu His Ala Trp Val Arg Glu Arg
    1040                1045                1050

Phe Tyr Gln Asp Lys Leu Arg Trp Asp Lys Cys Arg Tyr Tyr His
    1055                1060                1065

Asp Arg Tyr Thr Pro Leu Tyr Thr Ala Arg Asp Ala Arg Glu Trp
    1070                1075                1080

Arg Pro Leu His Gly Arg Glu His Asp Arg Leu Val Gln Ser Gly
    1085                1090                1095

Arg Pro Tyr Lys Asp Ser Tyr Trp Gly Arg Lys Gly Trp Glu Leu
    1100                1105                1110

Gln Ser Arg Gly Lys Glu Arg Pro His Phe Asn Ser Pro Arg Glu
    1115                1120                1125

Ala Pro Ser Leu Ala Val Pro Leu Glu Arg His Leu Gln Glu Lys
    1130                1135                1140

Ala Ala Leu Ser Val Gln Asp Ser Ser His Ser Leu Pro Glu Arg
    1145                1150                1155

Phe His Glu His Lys Ser Val Lys Ser Arg Lys Arg Arg Tyr Glu
    1160                1165                1170

Thr Leu Glu Asn Asn Asp Gly Arg Leu Glu Lys Lys Val His Lys
    1175                1180                1185

Ser Leu Glu Lys Asp Thr Leu Glu Glu Pro Arg Val Lys Lys His
    1190                1195                1200

Lys Lys Ser Lys Lys Lys Lys Ser Lys Asp Lys His Arg Asp
    1205                1210                1215

Arg Glu Ser Arg His Gln Gln Glu Ser Asp Phe Ser Gly Ala Tyr
    1220                1225                1230

Ser Asp Ala Asp Leu His Arg His Arg Lys Lys Lys Lys Lys Lys
    1235                1240                1245

Lys Arg His Ser Arg Lys Ser Glu Asp Phe Ile Lys Asp Val Glu
    1250                1255                1260

Met Arg Leu Pro Lys Leu Ser Ser Tyr Glu Ala Gly Gly His Phe
    1265                1270                1275

Arg Arg Thr Glu Gly Ser Phe Leu Leu Ala Asp Gly Leu Pro Val
    1280                1285                1290

Glu Asp Ser Gly Pro Phe Arg Glu Lys Thr Lys His Leu Arg Met
    1295                1300                1305

-continued

```
Glu Ser Arg Pro Asp Arg Cys Arg Leu Ser Glu Tyr Gly Gln Asp
    1310            1315            1320

Ser Thr Phe
    1325
```

HUMAN DEUBIQUITINATING PROTEASE GENE ON CHROMOSOME 7 AND ITS MURINE ORTHOLOG

BACKGROUND OF THE INVENTION

The role of ubiquitin in protein degradation was discovered and the main enzymatic reactions of this system elucidated in biochemical studies in a cell-free system from reticulocytes. In this system, proteins are targeted for degradation by covalent ligation to ubiquitin, a 76-amino-acid-residue protein. Briefly, ubiquitin-protein ligation requires the sequential action of three enzymes. The C-terminal Gly residue of ubiquitin is activated in an ATP-requiring step by a specific activating enzyme, E1 (Step 1). This step consists of an intermediate formation of ubiquitin adenylate, with the release of $PP_i$, followed by the binding of ubiquitin to a Cys residue of E1 in a thiolester linkage, with the release of AMP. Activated ubiquitin is next transferred to an active site Cys residue of a ubiquitin-carrier protein, E2 (Step 2). In the third step catalyzed by a ubiquitin-protein ligase or E3 enzyme, ubiquitin is linked by its C-terminus in an amide isopeptide linkage to an -amino group of the substrate protein's Lys residues (Step 3).

Proteins ligated to polyubiquitin chains are usually degraded by the 26S proteasome complex that requires ATP hydrolysis for its action. The 26S proteasome is formed by an ATP-dependent assembly of a 20S proteasome, a complex that contains the protease catalytic sites, with 19S "cap" or regulatory complexes. The 19S complexes contain several ATPase subunits and other subunits that are presumably involved in the specific action of the 26S proteasome on ubiquitinylated proteins. The roles of ATP in the assembly of the 26S proteasome complex and in its proteolytic action are not understood. The action of the 26S proteasome presumably generates several types of products: free peptides, short peptides still linked to ubiquitin via their Lys residues, and polyubiquitin chains (Step 4). The latter two products are converted to free and reusable ubiquitin by the action of ubiquitin-C-terminal hydrolases or isopeptidases (Steps 5 and 6). Some isopeptidases may also disassemble certain ubiquitin-protein conjugates (Step 7) and thus prevent their proteolysis by the 26S proteasome. The latter type of isopeptidase action may have a correction function to salvage incorrectly ubiquitinylated proteins or may have a regulatory role. Short peptides formed by the above processes can be further degraded to free amino acids by cytosolic peptidases (Step 8).

Ubiquitin-mediated degradation of protein is involved in various biological processes. The selective and programmed degradation of cell-cycle regulatory proteins, such as cyclins, inhibitors of cyclin-dependent kinases, and anaphase inhibitors are essential events in cell-cycle progression. Cell growth and proliferation are further controlled by ubiquitin-mediated degradation of tumor suppressors, protooncogenes, and components of signal transduction systems. The rapid degradation of numerous transcriptional regulators is involved in a variety of signal transduction processes and responses to environmental cues. The ubiquitin system is clearly involved in endocytosis and down-regulation of receptors and transporters, as well as in the degradation of resident or abnormal proteins in the endoplasmic reticulum. There are strong indications for roles of the ubiquitin system in development and apoptosis, although the target proteins involved in these cases have not been identified. Dysfunction in several ubiquitin-mediated processes causes pathological conditions, including malignant transformation.

Our knowledge of different signals in proteins that mark them for ubiquitinylation is also limited. Recent reports indicate that many proteins are targeted for degradation by phosphorylation. It was observed previously that many rapidly degraded proteins contain PEST elements, regions enriched in Pro, Glu, Ser, and Thr residues. More recently, it was pointed out that PEST elements are rich in S/TP sequences, which are minimum consensus phosphorylation sites for Cdks and some other protein kinases. Indeed, it now appears that in several (though certainly not all) instances, PEST elements contain phosphorylation sites necessary for degradation. Thus multiple phosphorylations within PEST elements are required for the ubiquitinylation and degradation of the yeast G1 cyclins Cln3 and Cln2, as well as the Gcn4 transcriptional activator. Other proteins, such as the mammalian G1 regulators cyclin E and cyclin D1, are targeted for ubiquitinylation by phosphorylation at specific, single sites. In the case of the IkBα inhibitor of the NF-kB transcriptional regulator, phosphorylation at two specific sites, Ser-32 and Ser-36, is required for ubiquitin ligation. β-cateinin, which is targeted for ubiquitin-mediated degradation by phosphorylation, has a sequence motif similar to that of IkBα around these phosphorylation sites. However, the homology in phosphorylation patterns of these two proteins is not complete, because phosphorylation of other sites of β-catenin is also required for its degradation. Other proteins targeted for degradation by phosphorylation include the Cdk inhibitor Sic1p and the STAT1 transcription factor. Though different patterns of phosphorylation target different proteins for degradation, a common feature appears to be that the initial regulatory event is carried out by a protein kinase, while the role of a ubiquitin ligase would be to recognize the phosphorylated form of the protein substrate. It further appears that different ubiquitin ligases recognize different phosphorylation patterns as well as additional motifs in the various protein substrates.

However, the identity of such E3s is unknown, except for some PULC-type ubiquitin ligases that act on some phosphorylated cell-cycle regulators in the budding yeast. The multiplicity of signals that target proteins for ubiquitin-mediated degradation (and of ligases that have to recognize such signals) is underscored by observations that the phosphorylation of some proteins actually prevents their degradation. Thus the phosphorylation of the c-Mos protooncogene on Ser3 and the multiple phosphorylations of c-Fos and c-Jun protooncogenes at multiple sites by MAP kinases suppress their ubiquitinylation and degradation.

In addition to the families of enzymes involved in conjugation of ubiquitin, a very large family of deubiquitinating enzymes has recently been identified from various organisms. These enzymes have several possible functions. First, they may have peptidase activity and cleave the products of ubiquitin genes. Ubiquitin is encoded by two distinct classes of genes. One is a polyubiquitin gene, which encodes a linear polymer of ubiquitins linked through peptide bonds between the C-terminal Gly and N-terminal Met of contiguous ubiquitin molecules. Each copy of ubiquitin must be released by precise cleavage of the peptide bond between Gly-76-Met-1 of successive ubiquitin moieties. The other class of ubiquitin genes encodes ubiquitin C-terminal extension proteins, which are peptide bond fusions between the C-terminal Gly of ubiquitin and N-terminal Met of the extension protein. To date, the extensions described are ribosomal proteins consisting of 52 or 76–80 amino acids.

These ubiquitin fusion proteins are processed to yield ubiquitin and the corresponding C-terminal extension proteins. Second, deubiquitinating enzymes may have isopeptidase activities. When a target protein is degraded, deubiquitinating enzymes can cleave the polyubiquitin chain from the target protein or its remnants. The polyubiquitin chain must also be disassembled by deubiquitinating enzymes during or after proteolysis by the 26 S proteasome, regenerating free monomeric ubiquitin. In this way, deubiquitinating enzymes can facilitate the ability of the 26 S proteasome to degrade ubiquitinated proteins. Third, deubiquitinating enzymes may hydrolyze ester, thiolester, and amide linkages to the carboxyl group of Gly-76 of ubiquitin. Such nonfunctional linkages may arise from reactions between small intracellular compounds such as glutathione and the E1-, E2-, or E3-ubiquitin thiolester intermediates. Fourth, deubiquitinating enzymes may compete with the conjugating system by removing ubiquitin from protein substrates, thereby rescuing them from degradation or any other function mediated by ubiquitination. Thus generation of ubiquitin by deubiquitinating enzymes from the linear polyubiquitin and ubiquitin fusion proteins and from the branched polyubiquitin ligated to proteins should be essential for maintaining a sufficient pool of free ubiquitin. Many deubiquitinating enzymes exist, suggesting that these deubiquitinating enzymes recognize distinct substrates and are therefore involved in specific cellular processes. Although there is recent evidence to support such specificity of these deubiquitinating enzymes, the structure-function relationships of these enzymes remain poorly studied.

Deubiquitinating enzymes can be divided broadly on the basis of sequence homology into two classes, the ubiquitin-specific processing protease (UBP or USP, also known as type 2 ubiquitin C-terminal hydrolase (type 2 UCH)) and the UCH, also known as type 1 UCH). UCH (type 1 UCH) enzymes hydrolyze primarily C-terminal esters and amides of ubiquitin but may also cleave ubiquitin gene products and disassemble polyubiquitin chains. They have in common a 210-amino acid catalytic domain, with four highly conserved blocks of sequences that identify these enzymes. They contain two very conserved motifs, the CYS and HIS boxes. Mutagenesis studies revealed that the two boxes play important roles in catalysis. Some UCH enzymes have significant C-terminal extensions. The functions of the C-terminal extensions are still unknown but appear to be involved in proper localization of the enzyme. The active site of these UCH enzymes contains a catalytic triad consisting of cysteine, histidine, and aspartate and utilizes a chemical mechanism similar to that of papain. The crystal structure of one of these, UCH-L3, has been solved at 1.8 Å resolution. The enzyme comprises a central antiparallel β-sheet flanked on both sides by helices. The β-sheet and one of the helices are similar to those observed in the thiol protease cathepsin B. The similarity includes the three amino acid residues that comprise the active site, $Cys^{95}$, $His^{169}$, and $Asp^{184}$. The active site appears to fit the binding of ubiquitin that may anchor also at an additional site. The catalytic site in the free enzyme is masked by two different segments of the molecule that limit nonspecific hydrolysis and must undergo conformational rearrangement after substrate binding.

UBP (type 2 UCH) enzymes are capable of cleaving the ubiquitin gene products and disassembling polyubiquitin chains after hydrolysis. It appears that there is a core region of about 450 amino acids delimited by CYS and HIS boxes. Many of these isoforms have N-terminal extensions and a few have C-terminal extensions. In addition, there are variable sequences in the core region of many of the isoforms. The functions of these divergent sequences remain poorly characterized. Another interesting function of specific UBPs is the regulation of cell proliferation. It was observed that cytokines induced in T-cells specific deubiquitinating enzymes (DUBs), termed DUB-1 and DUB-2. DUB-1 is induced by stimulation of the cytokine receptors for IL-3, IL-5, and GM-CSF, suggesting a role in its induction for the β-common (betac) subunit of the interleukin receptors. Overexpression of a dominant negative mutant of JAK2 inhibits cytokine induction of DUB-1, suggesting that the regulation of the enzyme is part of the cell response to the JAK/STAT signal transduction pathway. Continued expression of DUB-1 arrests cells at $G_1$; therefore, the enzyme appears to regulate cellular growth via control of the $G_0$–$G_1$ transition. The catalytic conserved Cys residue of the enzyme is required for its activity. DUB-2 is induced by IL-2 as an immediate early (IE) gene that is down-regulated shortly after the initiation of stimulation. The function of this enzyme is also obscure. It may stimulate or inhibit the degradation of a critical cell-cycle regulator.

Cytokines, such as interleukin-2 (IL-2), activate intracellular signaling pathways via rapid tyrosine phosphorylation of their receptors, resulting in the activation of many genes involved in cell growth and survival. The deubiquitinating enzyme DUB-2 is induced in response to IL-2 and is expressed in human T-cell lymphotropic virus-I (HTLV-1)-transformed T cells that exhibit constitutive activation of the IL-2 JAK/STAT (signal transducers and activators of transcription) pathway, and when expressed in Ba/F3 cells DUB-2 markedly prolonged IL-2-induced STAT5 phosphorylation. Although DUB-2 does not enhance IL-2-mediated proliferation, when withdrawn from growth factor, cells expressing DUB-2 had sustained STAT5 phosphorylation and enhanced expression of IL-2-induced genes cis and c-myc. DUB-2 expression markedly inhibited apoptosis induced by cytokine withdrawal allowing cells to survive. Therefore, DUB-2 has a role in enhancing signaling through the JAK/STAT pathway, prolonging lymphocyte survival, and, when constitutively expressed, may contribute to the activation of the JAK/STAT pathway observed in some transformed cells. (Migone, T.-S., et al., *Blood*. 2001;98: 1935–1941).

Protein ubiquitination is an important regulator of cytokine-activated signal transduction pathways and hematopoietic cell growth. Protein ubiquitination is controlled by the coordinate action of ubiquitin-conjugating enzymes and deubiquitinating enzymes. Recently a novel family of genes encoding growth-regulatory deubiquitinating enzymes (DUB-1 and DUB-2) has been identified. DUBs are immediate-early genes and are induced rapidly and transiently in response to cytokine stimuli. By means of polymerase chain reaction amplification with degenerate primers for the DUB-2 complementary DNA, 3 murine bacterial artificial chromosome (BAC) clones that contain DUB gene sequences were isolated. One BAC contained a novel DUB gene (DUB-2A) with extensive homology to DUB-2. Like DUB-1 and DUB-2, the DUB-2A gene consists of 2 exons. The predicted DUB-2A protein is highly related to other DUBs throughout the primary amino acid sequence, with a hypervariable region at its C-terminus. In vitro, DUB-2A had functional deubiquitinating activity; mutation of its conserved amino acid residues abolished this activity. The 5' flanking sequence of the DUB-2A gene has a hematopoietic-specific functional enhancer sequence. It is proposed that there are at least 3 members of the DUB subfamily (DUB-1, DUB-2, and DUB-2A) and that different hematopoietic cytokines induce specific DUB genes, thereby initiating a cytokine-specific growth response. (Baek, K.-H., et al, *Blood.* 2001;98:636–642).

Protein ubiquitination also serves regulatory functions in the cell that do not involve proteasome-mediated degradation. For example, Hicke and Riezman have recently demonstrated ligand-inducible ubiquitination of the Ste2 receptor in yeast. Ubiquitination of the Ste2 receptor triggers receptor endocytosis and receptor targeting to vacuoles, not proteasomes. Also, Chen et al. have demonstrated that activation of the IB kinase requires a rapid, inducible ubiquitination event. This ubiquitination event is a prerequisite for the specific phosphorylation of IB and does not result in subsequent proteolysis of the kinase complex. The ubiquitination of Ste2 and IB kinase appears reversible, perhaps resulting from the action of a specific deubiquitinating enzyme.

A large superfamily of genes encoding deubiquitinating enzymes, or UBPs, has recently been identified. UBPs are ubiquitin-specific thiol-proteases that cleave either linear ubiquitin precursor proteins or post-translationally modified proteins containing isopeptide ubiquitin conjugates. The large number of UBPs suggests that protein ubiquitination, like protein phosphorylation, is a highly reversible process that is regulated in the cell.

Interestingly, UBPs vary greatly in length and structural complexity, suggesting functional diversity. While there is little amino acid sequence similarity throughout their coding region, sequence comparison reveals two conserved domains. The Cys domain contains a cysteine residue that serves as the active enzymatic nucleophile. The His domain contains a histidine residue that contributes to the enzyme's active site. More recent evidence demonstrates six homology domains contained by all members of the ubp superfamily. Mutagenesis of conserved residues in the Cys and His domains has identified several residues that are essential for UBP activity.

Recently, a growth regulatory deubiquitinating enzyme, DUB-1, that is rapidly induced in response to cytokine receptor stimulation was identified. DUB-1 is specifically induced by the receptors for IL-3, granulocyte macrophage-colony-stimulating factor, and IL-5, suggesting a specific role for the c subunit shared by these receptors. In the process of cloning the DUB-1 gene, a family of related, cross-hybridizing DUB genes was identified. From this, other DUB genes might be induced by different growth factors. Using this approach, an IL-2-inducible DUB enzyme, DUB-2 and closely related DUB-2a were identified. DUB-1 and DUB-2 are more related to each other than to other members of the ubp superfamily and thereby define a novel subfamily of deubiquitinating enzymes.

Hematopoietic-specific, cytokine induced DUBs in murine system have shown to prolong cytokine receptor, see Migone, T. S., et al. (2001). The deubiquitinating enzyme DUB-2 prolongs cytokine-induced signal transducers and activators of transcription activation and suppresses apoptosis following cytokine withdrawal, *Blood* 98, 1935–41; Zhu, Y., et al., (1997). DUB-2 is a member of a novel family of cytokine-inducible deubiquitinating enzymes, *J Biol Chem* 272, 51–7 and Zhu, Y., et al., (1996). The murine DUB-1 gene is specifically induced by the betac subunit of interleukin-3 receptor, *Mol Cell Biol* 16, 4808–17.). These effects are likely due to the deubiquitination of receptors or other signaling intermediates by DUB-1 or DUB-2, murine analogs of hDUBs. Inhibition of hDUBs may achieve down-regulation of specific cytokine receptor signaling, thus modulating specific immune responses.

Cytokines regulate cell growth by inducing the expression of specific target genes. A recently identified a cytokine-inducible, immediate-early gene, DUB-1, encodes a deubiquitinating enzyme with growth regulatory activity. In addition, a highly related gene, DUB-2, that is induced by interleukin-2 was identified. The DUB-2 mRNA was induced in T cells as an immediate-early gene and was rapidly down-regulated. Like DUB-1, the DUB-2 protein had deubiquitinating activity in vitro. When a conserved cysteine residue of DUB-2, required for ubiquitin-specific thiol protease activity, was mutated to serine (C60S), deubiquitinating activity was abolished. DUB-1 and DUB-2 proteins are highly related throughout their primary amino acid sequence except for a hypervariable region at their COOH terminus. Moreover, the DUB genes co-localize to a region of mouse chromosome 7, suggesting that they arose by a tandem duplication of an ancestral DUB gene. Additional DUB genes co-localize to this region, suggesting a larger family of cytokine-inducible DUB enzymes. We propose that different cytokines induce specific DUB genes. Each induced DUB enzyme thereby regulates the degradation or the ubiquitination state of an unknown growth regulatory factor, resulting in a cytokine-specific growth response.

On the basis of these structural criteria, additional members of the DUB subfamily can be identified in the GenBank™. The highest degree of homology is in the Cys and His domains. Additionally, this putative human DUB protein contains a Lys domain (amino acids 400–410) and a hypervariable region (amino acids 413–442).

Murine DUB (mDUB) subfamily members differ from other UBPs by functional criteria as well. mDUB subfamily members are cytokine-inducible, immediate-early genes and may therefore play regulatory roles in cellular growth or differentiation. Also, DUB proteins are unstable and are rapidly degraded by ubiquitin-mediated proteolysis shortly after their induction. mDUB reports demonstrate that specific cytokines, such as IL-2 and IL-3, induce specific deubiquitinating enzymes (DUBs). The DUB proteins may modify the ubiquitin-proteolytic pathway and thereby mediate specific cell growth or differentiation signals. These modifications are temporally regulated. The DUB-2 protein, for instance, is rapidly but transiently induced by IL-2. Interference of DUB enzymes with specific isopeptidase inhibitors may block specific cytokine signaling events.

The prior art teaches some partial sequences with homology to DUBs; specifically Human cDNA sequence SEQ ID NO: 17168 in EP1074617-A2; a human protease and protease inhibitor PPIM-4 encoding cDNA; in WO200110903-A2 and human ubiquitin protease 23431 coding sequence in WO200123589-A2.

REFERENCES

1. Baek, K. H., Mondoux, M. A., Jaster, R., Fire-Levin, E., and D'Andrea, A. D. (2001). DUB-2A, a new member of the DUB subfamily of hematopoietic deubiquitinating enzymes, Blood 98, 636–42.
2. Jaster, R., Baek, K. H., and D'Andrea, A. D. (1999). Analysis of cis-acting sequences and trans-acting factors regulating the interleukin-3 response element of the DUB-1 gene, Biochim Biophys Acta 1446, 308–16.
3. Jaster, R., Zhu, Y., Pless, M., Bhattacharya, S., Mathey-Prevot, B., and D'Andrea, A. D. (1997). JAK2 is required for induction of the murine DUB-1 gene, Mol Cell Biol 17, 3364–72.

4. Migone, T. S., Humbert, M., Rascle, A., Sanden, D., D'Andrea, A., Johnston, J. A., Baek, K. H., Mondoux, M. A., Jaster, R., Fire-Levin, E., et al. (2001). The deubiquitinating enzyme DUB-2 prolongs cytokine-induced signal transducers and activators of transcription activation and suppresses apoptosis following cytokine withdrawal, Blood 98, 1935–41.
5. Zhu, Y., Carroll, M., Papa, F. R., Hochstrasser, M., and D'Andrea, A. D. (1996a). DUB-1, a deubiquitinating enzyme with growth-suppressing activity, Proc Natl Acad Sci USA 93, 3275–9.
6. Zhu, Y., Lambert, K., Corless, C., Copeland, N. G., Gilbert, D. J., Jenkins, N. A., and D'Andrea, A. D. (1997). DUB-2 is a member of a novel family of cytokine-inducible deubiquitinating enzymes, J Biol Chem 272, 51–7.
7. Zhu, Y., Pless, M., Inhorn, R., Mathey-Prevot, B., and D'Andrea, A. D. (1996b). The murine DUB-1 gene is specifically induced by the betac subunit of interleukin-3 receptor, Mol Cell Biol 16, 4808–17.

Scott Emr described a role for monoubiquitination in protein sorting in the late endosome, which has a role in determining which proteins, both newly synthesized and endocytosed, will be delivered to the lumen of the vacuole and which to its limiting membrane. Proteins destined for lumen are sorted into internal vesicles at the multivesicular body (MVB) stage of endosome maturation, whereas proteins destined for the vacuolar membrane, or for recycling to the plasma membrane, remain in the endosome's limiting membrane. Emr showed that the sorting of a vacuolar hydrolase into MVB vesicles requires the monoubiqutination of this cargo molecule at a specific lysine residue (Katzmann et al., 2001). Thus, monoubiquitination is a green light for traffic to proceed from this important intracellular intersection to the lumen of the vacuole. The policeman directing the traffic is an endosome-localized protein complex called ESCRT-I, one of whose components, Vps23, plays a key role in recognizing the cargo's ubiquitin signal (Katzmann et al., 2001). Vps23 is one of a small family of UEV proteins (ubiquitin E2 variants) that resemble E2s but cannot perform canonical E2 functions. The ESCRT-I complex binds ubiquitin, and a mutation in Vps23 that cripples ubiquitin-dependent sorting in the MVB pathway abolishes ubiquitin binding to ESCRT-I. A model in which Vsp23 binds ubiquitin directly, while still inferential, received support from structural studies of a different UEV protein. Intriguingly, the mammalian homolog of Vps23, known as tsg101, is a tumor suppressor (Li and Cohen, 1996) The current results suggest that mutations in tsg101 could cause persistent signaling by growth factor receptors because of inappropriate receptor recycling to the plasma membrane, thus leading to tumorigenesis.

A role for monoubiquitination in triggering the first step of endocytosis—the internalization of plasma membrane proteins—is well established (Hicke, 2001), but how this signal is recognized has been unclear. Linda Hicke reported that yeast Ent1 is vital for the ubiquitin-dependent endocytosis of yeast factor receptor (see also Wendland et al., 1999). Ent1 carries a proposed ubiquitin binding motif called the UIM domain (Hofmann and Falquet, 2001), and Hicke showed that Ent1 indeed binds ubiquitin directly. Ent1 also binds clathrin (Wendland et al., 1999) and so is poised to link monoubiquitinated cargo molecules to the endocytic machinery. Hicke's and Emr's results suggest that the ability of monoubiquitin to signal two different trafficking outcomes relies in part on distinct localizations of the relevant signal-recognizing components—Ent1 resides at the plasma membrane, while ESCRT-I is associated with late endosomes.

Fanconi Anemia (FA) is a rare cancer susceptibility disorder associated with cellular sensitivity to DNA damage that can be caused by mutations in at least seven genes. Alan D'Andrea shed new light on the molecular basis of FA: monoubiquitination of a specific lysine residue in one FA protein, known as D2, requires the activities of four upstream FA genes and leads to the relocalization of D2 within the nucleus (Garcia-Higuera et al., 2001). In normal cells, monoubiquitination of D2 is strongly augmented following DNA damage and is strictly required for damage-associated targeting of D2 and BRCA1 to subnuclear foci. Thus, D2 monoubiquitination links an FA protein complex to the BRCA1 repair machinery. Although the downstream events in this pathway are still unclear, localization of the signal-recognizing factor(s) will likely be critical. This new function of ubiquitin carries a strong flavor of certain roles of Sumo-1, a UbL that has been implicated in protein targeting to specific subnuclear structures (Hochstrasser, 2000).

Polyubiquitin chains are well known as a signal for substrate destruction by 26S proteasomes. But there are several kinds of chains, linked through different lysines of ubiquitin, suggesting that different chains might be distinct signals (Pickart, 2000). James Chen provided rigorous proof of this hypothesis by showing that noncanonical polyubiqitination can activate phosphorylation—in contrast to numerous examples of the converse regulation (Hershko and Ciechanover, 1998). Postreplicative DNA repair and the activation of IkBα kinase (IKK) require chains linked through Lys63, rather than the Lys48-chains that usually signal proteasomal proteolysis. Chen found that Tak1 kinase is a downstream target of Lys63-chain signaling in the IKK activation pathway. The assembly of these chains depends on an unusual UEV/E2 complex and a RING finger protein, Traf6 (Deng et al., 2000). (The RING finger defines a large E3 family.) Modification of Traf6 with a Lys63-chain leads to the activation of Tak1, which in turn phosphorylates IKK (Wang et al., 2001). Activated IKK then phosphorylates IkBα and triggers its tagging with Lys48-chains. Only then do proteasomes enter the picture—they degrade IkBα and thereby free its partner, NFkB, to translocate to the nucleus and activate the expression of inflammatory response genes. Chen's results suggest that Traf6 is the target of the Lys63-chain, as well as a catalyst of its assembly. Indeed, many other RING E3s also self-modify-although the consequence is more apt to be suicide (cf. tagging with Lys48-chains) than the kind of personality change seen with Traf6 (Joazeiro and Weissman, 2000). It remains to be seen if a similar mechanism applies in DNA repair, where a different RING protein, the Rad5 helicase, binds to a related UEV/E2 complex (Ulrich and Jentsch, 2000). New genetic data reported by Helle Ulrich confirmed the central importance of Rad5 in Lys-63 chain signaling in DNA repair (Ulrich, 2001).

These reports suggest a variety of new functions of protein ubiquitination and its potential involvement of subcellular trafficking including nucleus and the lumen of the intracellular vesicles. Thus regulation of ubiquitination by deubiquitinating proteases in various subcellular localization is become a critical issue.

Recently, a number of proteins have been identified as capable of transducing, that is, moving across cellular and nuclear membranes in an energy-independent manner. Transducing sequences have been identified in proteins involved in circadian rhythm, such as human Period proteins. It is thought that these proteins move more freely through cellular and nuclear membranes, and that this movement permits concerted control. No other enzymes involved in the deubiquitination activities have been identified as being capable of transducing or having NLS until now.

The presence of an NLS at the C-terminal suggests that the hDUB7 and its murine ortholog, mDUB7, are capable of translocating to the nucleus, possibly by importin-dependent manner and that these DUBs have a role in deubiquitinating ubiquitinated nuclear proteins and/or ubiquitinated proteins that are translocated to the nucleus. This has never been identified before. Protein ubiquitination targets selectively to proteasome degradation and/or provides facilitating protein localization. Thus, nuclear protein deubiquitination may have a role in unique function in regulation of nuclearprotein degradation as well as nuclear protein localization. The same logic can be applied to the vesicular targeting of DUB7 by targeting sequence, regulating vesicular protein degradation as well as invloved in traficking of vesicular proteins.

REFERENCES

Katzmann D. J., Babst M. and Emr S. D. (2001) Ubiquitin-dependent sorting into the multivesicular body pathway requires the function of a conserved endosomal protein sorting complex, ESCRT-I. *Cell*, 106:145–155.

Li L. and Cohen S. N. (1996) tsg101: a novel tumor susceptibility gene isolated by controlled homozygous functional knockout of allelic loci in mammalian cells. *Cell*, 85:319–329.

Hicke L. (2001) A new ticket for entry into budding vesicles—ubiquitin. *Cell*, 106:527–530.

Wendland B., Steece K. E. and Emr S. D. (1999) Yeast epsins contain an essential N-terminal ENTH domain, bind clathrin, and are required for endocytosis. *EMBO J*, 18:4383–4393.

Hofmann K. and Falquet L. (2001) A ubiquitin-interacting motif conserved in components of the proteasomal and lysosomal protein degradation systems. *Trends Biochem. Sci.*, 26:347–350.

Garcia-Higuera I., Taniguchi T., Ganesan S., Meyn M. S., Timmers C., Hejna J., Grompe M. and D'Andrea A. D. (2001) Interaction of the Fanconi Anemia proteins and BRCA1 in a common pathway. *Mol. Cell*, 7:249–262.

Hochstrasser M. (2000) Evolution and function of ubiquitin-like protein-conjugation systems. *Nat. Cell Biol.*, 2:E153–E157.

Pickart C. M. (2000) Ubiquitin in chains. *Trends Biochem. Sci.*, 25:544–548.

Pickart C. M. (2000) Ubiquitin in chains. *Trends Biochem. Sci.*, 25:544–548.

Hershko A. and Ciechanover A. (1998) The ubiquitin system. *Annu. Rev. Biochem.*, 67:425–479.

Deng L., Wang C., Spencer E., Yang L., Braun A., You J., Slaughter C., Pickart C. and Chen Z. J. (2000) Activation of the IkB kinase complex by TRAF6 requires a dimeric ubiquitin-conjugating enzyme complex and a unique polyubiquitin chain. *Cell*, 103:351–361.

Wang C., Deng L., Hong M., Akkaraju G. R., Inoue J.-I. and Chen Z. J. (2001) TAK1 is a ubiquitin-dependent kinase of MKK and IKK. *Nature*, 412:346–351.

Joazeiro C. A. P. and Weissman A. M. (2000) RING finger proteins: mediators of ubiquitin ligase activity. *Cell*, 102:549–552.

Ulrich H. (2001) The srs2 suppressor of UV sensitivity acts specifically on the RAD5- and MMS2-dependent branch of the RAD6 pathway. *Nucleic Acids Res.*, 29:3487–3494.

Ulrich H. D. and Jentsch S. (2000) Two RING finger proteins mediate cooperation between ubiquitin-conjugating enzymes in DNA repair. *EMBO J.*, 19:3388–3397.

SUMMARY OF THE INVENTION

The present invention is directed to identification of human homolog of murine DUBs, hematopoietic-specific, cytokine-inducible deubiquitinating proteases found on chromosome 7, respective regulatory region and its murine ortholog, named as hDUB7 and mDUB7, respectively. Both hDUB7 and its murine ortholog mDUB7 were identified by searching human and mouse genome databases using murine DUB-1 and DUB-2 sequences. These genes (hDUB7 and mDUB7) share open reading frames (ORFs) that are 67% amino acid identity to each other, when gaps caused by deletion was not counted as mismatch, and exhibit 75% identity in nucleotide sequence. Furthermore, both hDUB7 and mDUB7 share 48% identity to murine DUBs, DUB1 and DUB2 within 297 amino acids core DUB sequences. In addition, hDUB7 and mDUB7 genes share open reading frames that are greater than 92% amino acid identity within 540 amino acids N-terminal ubiquitin protease domain (with 98.4% identity within 313 amino acid core). These genes also exhibit 74% identity within 138 amino acids C-terminal conserved domain containing several putative nuclear localization sequences (NLSs) and stretches of amino acid sequences that are known to possess transducing capacity (KAKKHKKSKKKKKSKDKHR and HRH-KKKKKKKKRHSRK)(SEQ ID No. 1 and SEQ ID No. 2, respectively.

Therefore, the present invention is also directed to a transducing peptide comprising an NLS or transducing sequence of hDUB7 or mDUB7 linked to a cargo molecule. The invention also includes a transducing peptide comprising an NLS or transducing sequence that is selected from the group consisting of peptidyl fragments comprising KAKKHKKSKKKKKSKDKHR, (SEQ ID No. 1) HRH-KKKKKKKKRHSRK, (SEQ ID No. 2) KKH-KKSKKKKKSKDKHR, (SEQ ID No. 3) and HRHRKKKKKKKRHSRK (SEQ ID No. 4). The invention also comprises a transducing peptide wherein the cargo molecule is a biologically active protein, therapeutically effective compound, antisense nucleotide, or test compound. The invention also includes a method of delivering a biologically active protein, therapeutically effective compound, antisense nucleotide, or test compound to a cell wherein a transducing peptide is added exogenously to a cell.

Manipulation of these gene products by small molecular compounds can (1) reduce inflammation by regulating proinflammatory cytokine signaling, (2) modulate autoimmune diseases by regulating cytokine receptor signaling that are critical for lymphocytes proliferation, and (3) immune over-reaction during infection using above mechanisms.

Search Methods for Identifying hDUB7 and mDUB7:

mDUB1 (U41636), mDUB2 (U70368), and mDUB2A (AF393637) DNA sequences were used to search against nr (All non-redundant GenBank CDS translations+PDB+SwissProt+PIR+PRF) in GenBank for potential homologs. Homology was found to a cDNA (AK022759) whose C terminal was incomplete (3660 nucleotides capable of expressing 1197 amino acids run-off translation). In order to in silico clone the full length. Both EST extending and genomic sequence annotation methods were used. Sequence of AK022759 was searched against human ESTs and genomic sequences. AK022759 was extended manually based on matching ESTs and mapped genomic sequence on contig NT_007844.8 from chromosome 7. From these full-length sequence for open reading frame for hDUB7 was generated (3951 nucleotides long DNA segment capable of generating 1316 amino acids long polypeptide).

For in silico cloning of the putative full length of mDUB7, hDUB7 amino acid sequence was used to search against nr by blastp. The highest match to Mouse proteins is a protein similar to mDUB2. The accession number for this protein is BAB27190 and for nucleotide sequence is AK010801 (1485 nucleotide long capable of translating 487 amino acids run-on translation). Based on Genbank annotation, the gene has partial sequence with C terminal incomplete. In order to get the full length of mDUB7, nucleotide sequence of AK010801 was used to search against Mouse Genomic sequence. There was no match to Mouse curated NT contigs database and match was found on contig_70795 from Mouse Arachne_Nov30 database (preliminary assembly of the mouse WGS reads based on an Nov 9th freeze of the WGS data) in Genbank. Putative genes from contig_70795 were annotated by GENSCAN prediction. There is one putative protein with extended/finished C terminal aligned perfectly with BAB27190 except having 33 amino acids missing in the middle of sequence. The nucleotide sequence of the 33 amino acids segment from BAB27190 was searched against the Mouse genomic sequence and found it matched to the genomic sequence region that generates the putative full length mDUB7 and has potential splice sites on the borders. It implies that exon was missed by GENSCAN annotation. A full length mouse DUB7 was constructed by adding 33 amino acids to the putative protein according to the genomic sequence alignment (3981 nucleotides long open reading frame capable of generating 1326 amino acids long polypeptide). The final mDUB7 sequence was aligned with hDUB7 and showed 67% homology in amino acid level and 75% homology in nucleotide level.

TaqMan Real Time PCR Analysis of Expression of hDUB7 in Human Immunocytes Upon Various Stimulation Protocol of reverse transcription (RT) from total cellular RNA using random hexamer as primer (using TaqMan Reverse Transcription Reagents Cat# N808-0234)

1 ug of total RNA preparation in 100 ul of 1× TaqMan RT Buffer Mix, 5.5 mM MgCl$_2$, 0.5 mM dNTPs, 2.5 uM Random Hexamers, 40 U RNAse inhibitor, 125U Multiscribe Reverse Transcriptase. Mix by pipeting up and down. Incubate 25° C. for 10 minutes (annealing step), 48° C. for 30 minutes (reverse transcription), and 95° C. for 5 minutes (heat killing of the enzyme). The samples can be left at the machine at 4° C., or alternatively, can be stored at −20° C. Yield of cDNA synthesis can be measured by incorporation of small portion of radioactive dATP (or dCTP). Average efficiency for this protocol is between 60–80% of conversion of RNA to cDNA.

Protocol of TaqMan Real-Time Quantitative PCR 1 ul of TaqMan RT product in 12.5 ul of 1× master Mix (Applied Biosystems Cat# 4304437) containing all necessary reaction components except primers and probes, 0.9 uM forward primer, 0.9 uM reverse primer, 0.2 uM probe. Mix by pipetting up and down. Samples containing GADPH primer pair and probe were also prepared as control. Thermal cycling and detection of the real-time amplification were performed using the ABI PRISM 7900HT Sequuence Detection System. The quantity of target gene is given relative to the GADPH control based on $C_t$ values determined during the exponential phase of PCR.

Primer-probe set used is as follow:

Forward Primer (SEQ ID No.5)
5'-CCACGACAGAACTGCACTTGTAG-3'

Reverse Primer (SEQ ID No.6)
5'-CCGGGACTTTCCATTTTCG-3'

Probe sequence (SEQ ID No.5)
5'-CAACTGTAACCTCTCTGATCGGTTTCAC-GAA-3'

TABLE 1

Expression of hDUB7 in PBMC stimulated with LPS
(100 ng/ml) for 1.5, 7 and 24 hours by TaqMan (Donor 1).

| | LPS Stimulation/Time | | |
| --- | --- | --- | --- |
| | 1.5 hours | 7 hours | 24 hours |
| Fold Upregulation upon stimulation | 0.9 | 1.5 | 1.0 |

TABLE 2

Expression of DUB7 in PBMC stimulated with LPS
(100 ng/ml) and/or PHA (5 ug/ml)
for 1.5, 7, 24 hours by TaqMan (donor 2, donor 3)

| | Fold Upregulation upon stimulation | | |
| --- | --- | --- | --- |
| | LPS | PHA | LPS + PHA |
| Donor 2 Stimuli/time | | | |
| 1.5 hours | 1.1 | 1.2 | 1.1 |
| 7 hours | 3.3 | 9.2 | 9.2 |
| 24 hours | 0.2 | 0.3 | 0.3 |
| Donor 3 Stimuli/time | | | |
| 1.5 hours | 1.2 | 1.0 | 1.2 |
| 7 hours | 3.5 | 8.2 | 9.3 |
| 24 hours | 0.5 | 0.5 | 0.6 |

TABLE 3

Expression of hDUB7 in enriched B cells stimulated with LPS
(100 ng/ml) or IL-4 and anti-CD40 mAb for 4 and 20 hours
by TaqMan (Donor 4).

| | Fold Upregulation upon stimulation | |
| --- | --- | --- |
| Donor 4 Stimuli/time | LPS | IL-4, anti-CD40 mAb |
| 4 hours | 1.11 | 2.44 |
| 20 hours | 0.70 | 1.0 |

TABLE 4

Expression of hDUB7 in entiched CD4+ T cells
stimulated with anti-CD3 and anti-
CD3 mAbs for 3,6 and 18 hours by TaqMan (Donor 5).

| | mAbs Stimulation/Time | | |
|---|---|---|---|
| | 3 hours | 6 hours | 18 hours |
| Fold Upregulation upon stimulation | 1.36 | 1.74 | 0.37 |

TABLE 5

Expression of hDUB7 in differentiated Th0, Th1 and Th2
CD4+ T cells (Day 4 after
differentiation) stimulated with anti-CD3 and
anti-CD28 mAbs for 8 hours by TaqMan
(Donor 6).

| mAbs Stimulation | Th0 | Th1 | Th2 |
|---|---|---|---|
| Fold Upregulation upon stimulation | 2.60 | 0.36 | 1.72 |

TABLE 6

Expression of hDUB7 in differentiated Th0, Th1 and Th2
CD4+ T cells (Day 7 after
differentiation) stimulated with anti-CD3 and
anti-CD28 mAbs for 8 and 18 hours by TaqMan
(Donor 6).

| mAbs Stimulation | Th0 | Th1 | Th2 |
|---|---|---|---|
| Fold Upregulation in 8 hours | 1.38 | 1.11 | 1.71 |
| Fold Upregulation in 18 hours | 0.94 | 0.81 | 1.47 |

TABLE 7

Expression of hDUB7 in various tissue examined
by Affymatrix chip analysis

| Tissue | Relative Intensity |
|---|---|
| Con_Adipose_1 | 2287 |
| Con_Adipose_2 | 4190 |
| CV_Heart_1 | 2545 |
| CV_Heart_2 | 3907 |
| CV_Heart_3 | 5367 |
| CV_Pericardia_1 | 3682 |
| Dig_Colon_1 | 2387 |
| Dig_Colon_2 | 2894 |
| Dig_Esophagus_1 | 5004 |
| Dig_Esophagus_2 | 1658 |
| Dig_FetalLiver_1 | 1288 |
| Dig_FetalLiver_2 | 4676 |
| Dig_FetalLiver_3 | 829 |
| Dig_FetalLiver_4 | 3161 |
| Dig_Liver_1 | 3094 |
| Dig_Liver_2 | 1527 |
| Dig_Liver_3 | 3410 |
| Dig_Pancreas_1 | 3731 |
| Dig_Pancreas_2 | 4837 |
| Dig_Rectum_1 | 2329 |
| Dig_Rectum_2 | 1851 |
| Dig_SalivaryGland_1 | 2337 |
| Dig_SalivaryGland_2 | 2110 |
| Dig_SmallIntestine_1 | 2838 |
| Dig_SmallIntestine_2 | 2662 |
| Dig_Stomach_1 | 2187 |
| End_AdrenalGland_1 | 591 |
| End_AdrenalGland_2 | 2199 |
| End_Thyroid_1 | 2564 |
| End_Thyroid_2 | 2392 |
| End_Thyroid_3 | 3522 |
| Exo_Breast_1 | 3673 |
| Exo_Breast_2 | 6173 |
| Exo_MammaryGland_1 | 3741 |
| Imm_BoneMarrow_1 | 1090 |
| Imm_Spleen_1 | 2429 |
| Imm_Thymus_1 | 3666 |
| Imm_Thymus_2 | 1759 |
| Rep_Cervix_1 | 4482 |
| Rep_Cervix_2 | 3362 |
| Rep_Placenta_1 | 1248 |
| Rep_Placenta_2 | 2378 |
| Rep_Placenta_3 | 1622 |
| Rep_Prostate_1 | 5128 |
| Rep_Prostate_2 | 2762 |
| Rep_Testis_1 | 2252 |
| Rep_Testis_2 | 3196 |
| Rep_Uterus_1 | 4720 |
| Rep_Uterus_2 | 3789 |
| Res_Lung_1 | 2313 |
| Res_Lung_2 | 3177 |
| Res_Lung_3 | 4409 |
| Res_Lung_4 | 2366 |
| Res_Trachea_1 | 2152 |
| Res_Trachea_2 | 2358 |
| Res_Trachea_3 | 812 |
| Res_Trachea_4 | 812 |
| Sk_SkeletalMuscle_1 | 2838 |
| Sk_SkeletalMuscle_2 | 6106 |
| Skin_Skin_1 | 5500 |
| Uri_Kidney_1 | 3593 |
| Uri_Kidney_2 | 1311 |
| Uri_Kidney_3 | 2747 |
| Uri_Kidney_4 | 1530 |
| NS_Brain_1 | 3214 |
| NS_Brain_2 | 2173 |
| NS_Brain_3 | 1332 |
| NS_Brain_4 | 2604 |
| NS_Brain_5 | 1663 |
| NS_Cerebellum_1 | 3175 |
| NS_Cerebellum_2 | 1766 |
| NS_FetalBrain_1 | 4299 |
| NS_FetalBrain_2 | 2549 |
| NS_FetalBrain_3 | 4027 |
| NS_SpinalCord_1 | 2976 |
| NS_SpinalCord_2 | 3999 |
| NS_SpinalCord_3 | 4614 |

TABLE 8

Expression of mDUB7 in various tissue examined
by Affymatrix chip analysis

| Mouse # | Organ | Relative Intentisty |
|---|---|---|
| A | stomach | 56 |
| A | stomach | 11 |
| B | stomach | 175 |
| B | stomach | 97 |
| C | stomach | 178 |
| C | stomach | 126 |
| A | lymph | 516 |
| A | lymph | 365 |
| B | lymph | 494 |
| B | lymph | 335 |
| C | lymph | 475 |
| C | lymph | 509 |
| A | thymus | 913 |
| A | thymus | 1015 |
| B | thymus | 881 |

TABLE 8-continued

Expression of mDUB7 in various tissue examined by Affymatrix chip analysis

| Mouse # | Organ | Relative Intenisty |
|---|---|---|
| B | thymus | 927 |
| C | thymus | 834 |
| C | thymus | 975 |
| A | prostate | 327 |
| A | prostate | 350 |
| B | prostate | 75 |
| B | prostate | 423 |
| C | prostate | 405 |
| C | prostate | 267 |
| A | uterus | 549 |
| A | uterus | 372 |
| B | uterus | 225 |
| B | uterus | 418 |
| C | uterus | 335 |
| C | uterus | 401 |

Deubiquitination Assay

Confirmation that the DUB is a deubiquitinating enzyme may be shown using previously identified deubiquitination assay of ubiquitin—galactosidase fusion proteins, as described previously in the literature. Briefly, a fragment of the DUB, of approximately 1,500 nucleotides, based on the wild-type DUB cDNA (corresponding to amino acids 1 to about 500) and a cDNA containing a missense mutation are generated by PCR and inserted, in frame, into pGEX (Pharmacia), downstream of the glutathione S-transferase (GST) coding element. Ub-Met—gal is expressed from a pACYC184-based plasmid. Plasmids are co-transformed as indicated into MC 1061 Escherichia coli. Plasmid-bearing E. coli MC 1061 cells are lysed and analyzed by immunoblotting with a rabbit anti—gal antiserum (Cappel), a rabbit anti-GST antiserum (Santa Cruz), and the ECL system (Amersham Corp.). in vitro deubiquitinating enzyme activity may be shown from purified hDUB fusion protein using commercial polyubiquitinated protein as substrate.

HDUB7 and mDUB7 are Potential Inflamatory Cytokins Specific Immediate-Early Genes mDUB-1 was originally cloned as an IL-3-inducible immediate-early gene. Similarly, mDUB-2 was cloned as an IL-2-inducible immediate-early gene. We examined inducibility as well as cell-type specific expression of these genes using Affymatrix-Chip analysis and multiple TaqMan analysis from human organ RNA samples and human immunocytes RNA samples. Our data suggest that expression of hDUB7 are not apparent in monoocytes and other myoloid cell types but high in fresh human PBMC from several donor. Furthermore, enriched cell populations of several lymphocytes, including B cells, CD4+ T cells of Th-1 and Th-2 differentiation conditions as well as bulk CD4+ T cells showed significant upregulation upon appropriate stimulations. Currently, we can not rule out the possibility of upregulation upon stimulation in CD8+ T cells and potentially NK/NK-T cells.

The DUB Subfamily of the ubp Superfamily

From these data we propose that hDUB4s and hDUB8s are members of a discrete subfamily of deubiquitinating enzymes that shows the strongest similarity to mDUB subfamily including mDUB1, mDUB2, and mDUB2A, called the DUB subfamily. DUB subfamily members contain distinct structural features that distinguish them from other ubps. First, DUB subfamily members are comparatively small enzymes of approximately 500–550 amino acids. Second, DUB subfamily members share amino acid similarity not only in the Cys and His domains but also throughout their primary amino acid sequence. For instance, DUB proteins contain a lysine-rich region (Lys domain) and a HV domain near their carboxyl terminus.

The regulatory regions, or promoter regions, of each of the hDUB7 was analyzed for putative transcription factor binding motifs using TRANSFACFind, a dynamic programming method, see Heinemeyer, T., et al., "Expanding the TRANSFAC database towards an expert system of regulatory molecular mechanisrs" Nucleic Acids Res. 27, 318–322, (1999). The Transfac database provides eukaryotic cis- and trans-acting regulatory elements. The data is shown as table X.

TABLE 9 putative transcription factor binding motifs within the hDUB7 regulatory or promoter region. The position is indicated by nucleotides used in the table 9.

| Transfac | Position(Score) | Name | Description |
|---|---|---|---|
| M00148 | 1960 . . . 1966(100) | SRY | sex-determining region Y gene product |
|  | 876 . . . 870(100) |  |  |
|  | 1357 . . . 1351(92) |  |  |
|  | 1881 . . . 1875(92) |  |  |
|  | 1749 . . . 1755(90) |  |  |
|  | 118 . . . 124(90) |  |  |
|  | 267 . . . 261(90) |  |  |
|  | 275 . . . 269(90) |  |  |
|  | 1663 . . . 1669(90) |  |  |
|  | 1313 . . . 1319(90) |  |  |
|  | 1860 . . . 1854(90) |  |  |
|  | 108 . . . 114(90) |  |  |
| M00240 | 491 . . . 497(100) | Nkx-2.5 | homeo domain factor Nkx-2.5/Csx, tinman homolog |
|  | 1512 . . . 1506(90) |  |  |
|  | 1894 . . . 1888(90) |  |  |
| M00028 | 1844 . . . 1848(100) | HSF | heat shock factor (Drosophila) |
|  | 1835 . . . 1839(100) |  |  |
|  | 251 . . . 247(100) |  |  |
|  | 265 . . . 261(100) |  |  |
|  | 273 . . . 269(100) |  |  |

TABLE 9-continued putative transcription factor binding motifs within the hDUB7 regulatory or promoter region. The position is indicated by nucleotides used in the table 9.

| Transfac | Position(Score) | Name | Description |
|---|---|---|---|
|  | 1429 . . . 1433(100) |  |  |
|  | 1315 . . . 1319(100) |  |  |
|  | 1264 . . . 1268(100) |  |  |
|  | 1060 . . . 1064(100) |  |  |
|  | 1014 . . . 1010(100) |  |  |
|  | 1540 . . . 1536(100) |  |  |
|  | 1559 . . . 1555(100) |  |  |
|  | 1619 . . . 1615(100) |  |  |
|  | 110 . . . 114(100) |  |  |
|  | 66 . . . 70(100) |  |  |
|  | 1950 . . . 1946(100) |  |  |
|  | 1737 . . . 1741(95) |  |  |
|  | 1635 . . . 1639(95) |  |  |
|  | 651 . . . 647(95) |  |  |
|  | 1103 . . . 1107(95) |  |  |
|  | 1082 . . . 1078(95) |  |  |
|  | 16 . . . 20(95) |  |  |
|  | 1674 . . . 1678(94) |  |  |
|  | 1189 . . . 1185(94) |  |  |
|  | 880 . . . 876(91) |  |  |
| M00029 | 247 . . . 243(100) | HSF | heat shock factor (yeast) |
|  | 1667 . . . 1671(100) |  |  |
|  | 1210 . . . 1206(100) |  |  |
|  | 1745 . . . 1741(100) |  |  |
|  | 71 . . . 75(100) |  |  |
|  | 1844 . . . 1848(96) |  |  |
|  | 1835 . . . 1839(96) |  |  |
|  | 265 . . . 261(96) |  |  |
|  | 273 . . . 269(96) |  |  |
|  | 1429 . . . 1433(96) |  |  |
|  | 1315 . . . 1319(96) |  |  |
|  | 1264 . . . 1268(96) |  |  |
|  | 1060 . . . 1064(96) |  |  |
|  | 1014 . . . 1010(96) |  |  |
|  | 1540 . . . 1536(96) |  |  |
|  | 1559 . . . 1555(96) |  |  |
|  | 1619 . . . 1615(96) |  |  |
|  | 110 . . . 114(96) |  |  |
|  | 1950 . . . 1946(96) |  |  |
|  | 1674 . . . 1678(95) |  |  |
|  | 1189 . . . 1185(95) |  |  |
|  | 1737 . . . 1741(93) |  |  |
|  | 1635 . . . 1639(93) |  |  |
|  | 651 . . . 647(93) |  |  |
|  | 1103 . . . 1107(93) |  |  |
|  | 1082 . . . 1078(93) |  |  |
|  | 16 . . . 20(93) |  |  |
|  | 1120 . . . 1124(90) |  |  |
|  | 139 . . . 143(90) |  |  |
| M00101 | 1418 . . . 1412(100) | CdxA | CdxA |
|  | 1689 . . . 1695(98) |  |  |
|  | 1566 . . . 1572(98) |  |  |
|  | 1460 . . . 1466(98) |  |  |
|  | 1319 . . . 1325(98) |  |  |
|  | 969 . . . 975(98) |  |  |
|  | 1463 . . . 1457(98) |  |  |
|  | 1614 . . . 1608(98) |  |  |
|  | 1065 . . . 1059(94) |  |  |
|  | 1599 . . . 1605(93) |  |  |
|  | 1375 . . . 1369(93) |  |  |
|  | 1840 . . . 1834(93) |  |  |
|  | 1859 . . . 1865(92) |  |  |
|  | 1168 . . . 1174(92) |  |  |
|  | 1218 . . . 1212(92) |  |  |
|  | 1478 . . . 1484(90) |  |  |
| M00048 | 447 . . . 452(100) | ADR1 | alcohol dehydrogenase gene regulator 1 |
|  | 535 . . . 540(95) |  |  |
|  | 1716 . . . 1721(93) |  |  |
|  | 459 . . . 454(93) |  |  |
|  | 558 . . . 553(93) |  |  |
|  | 1180 . . . 1185(93) |  |  |
|  | 305 . . . 310(93) |  |  |
|  | 38 . . . 43(92) |  |  |

TABLE 9-continued putative transcription factor binding motifs within
the hDUB7 regulatory or promoter region.
The position is indicated by nucleotides used in the table 9.

| Transfac | Position(Score) | Name | Description |
|---|---|---|---|
| M00354 | 1951 . . . 1941(99) | Dof3 | Dof3 - single zinc finger transcription factor |
|  | 1560 . . . 1550(95) |  |  |
|  | 104 . . . 114(93) |  |  |
|  | 65 . . . 75(91) |  |  |
| M00227 | 1920 . . . 1928(98) | v-Myb | v-Myb |
| M00141 | 521 . . . 513(98) | Lyf-1 | LyF-1 |
|  | 828 . . . 820(98) |  |  |
| M00344 | 806 . . . 795(98) | RAV1 | 3'-part of bipartite RAV1 binding site, |
|  | 806 . . . 817(92) |  | interacting with AP2 domain |
|  | 1949 . . . 1960(92) |  |  |
| M00253 | 1139 . . . 1146(98) | cap | cap signal for transcription initiation |
|  | 681 . . . 688(96) |  |  |
|  | 374 . . . 381(96) |  |  |
|  | 299 . . . 306(95) |  |  |
|  | 1674 . . . 1667(94) |  |  |
|  | 1737 . . . 1730(91) |  |  |
|  | 31 . . . 24(91) |  |  |
|  | 16 . . . 9(91) |  |  |
|  | 1701 . . . 1694(91) |  |  |
|  | 1909 . . . 1902(90) |  |  |
|  | 619 . . . 626(90) |  |  |
|  | 1368 . . . 1375(90) |  |  |
| M00286 | 577 . . . 564(97) | GKLF | gut-enriched Krueppel-like factor |
|  | 271 . . . 258(96) |  |  |
| M00199 | 684 . . . 676(96) | AP-1 | AP-1 binding site |
|  | 676 . . . 684(95) |  |  |
| M00183 | 227 . . . 218(96) | c-Myb | c-Myb |
|  | 28 . . . 37(95) |  |  |
|  | 1247 . . . 1238(90) |  |  |
| M00154 | 1714 . . . 1721(96) | STRE | stress-response element |
| M00140 | 1824 . . . 1831(96) | Bcd | Bicoid |
|  | 834 . . . 841(93) |  |  |
|  | 527 . . . 534(93) |  |  |
| M00100 | 1418 . . . 1412(96) | CdxA | CdxA |
|  | 1209 . . . 1215(92) |  |  |
|  | 1348 . . . 1354(91) |  |  |
| M00291 | 1652 . . . 1667(95) | Freac-3 | Fork head RElated ACtivator-3 |
| M00073 | 1948 . . . 1958(95) | deltaEF1 | deltaEF1 |
|  | 807 . . . 797(95) |  |  |
|  | 1452 . . . 1442(92) |  |  |
|  | 805 . . . 815(90) |  |  |
| M00216 | 1176 . . . 1167(95) | TATA | Retroviral TATA box |
| M00120 | 1952 . . . 1942(95) | dl | dorsal |
|  | 1561 . . . 1551(93) |  |  |
| M00042 | 1861 . . . 1852(95) | Sox-5 | Sox-5 |
|  | 1790 . . . 1781(91) |  |  |
| M00174 | 675 . . . 685(95) | AP-1 | activator protein 1 |
| M00230 | 1797 . . . 1808(95) | Skn-1 | maternal gene product |
| M00272 | 1024 . . . 1033(94) | p53 | tumor suppressor p53 |
|  | 1033 . . . 1024(94) |  |  |
| M00160 | 1862 . . . 1851(94) | SRY | sex-determining region Y gene product |
| M00022 | 111 . . . 120(94) | Hb | Hunchback |
|  | 436 . . . 427(91) |  |  |
|  | 584 . . . 575(91) |  |  |
| M00053 | 447 . . . 456(94) | c-Rel | c-Rel |
| M00249 | 1244 . . . 1256(93) | CHOP-C/EBPalpha | heterodimers of CHOP and C/EBPalpha |
| M00142 | 1367 . . . 1362(93) | NIT2 | activator of nitrogen-regulated genes |
|  | 1348 . . . 1343(91) |  |  |
| M00289 | 1670 . . . 1658(93) | HFH-3 | HNF-3/Fkh Homolog 3 (= Freac-6) |
| M00019 | 1381 . . . 1366(93) | Dfd | Deformed |
|  | 1593 . . . 1608(91) |  |  |
| M00147 | 1903 . . . 1912(92) | HSF2 | heat shock factor 2 |
| M00184 | 806 . . . 815(92) | MyoD | myoblast determining factor |
| M00345 | 225 . . . 218(92) | GAmyb | GA-regulated myb gene from barley |
| M00094 | 1658 . . . 1670(92) | BR-C | Broad-Complex Z4 |
|  | 1398 . . . 1386(90) |  |  |
| M00349 | 1200 . . . 1191(92) | GATA-2 | GATA-binding factor 2 |
| M00077 | 443 . . . 451(92) | GATA-3 | GATA-binding factor 3 |
| M00087 | 388 . . . 399(91) | Ik-2 | Ikaros 2 |
| M00099 | 1268 . . . 1283(91) | S8 | S8 |
| M00285 | 1399 . . . 1411(91) | TCF11 | TCF11/KCR-F1/Nrf1 homodimers |

TABLE 9-continued putative transcription factor binding motifs within
the hDUB7 regulatory or promoter region.
The position is indicated by nucleotides used in the table 9.

| Transfac | Position(Score) | Name | Description |
|---|---|---|---|
| M00241 | 1224 . . . 1217(91) | Nkx-2.5 | homeo domain factor Nkx-2.5/Csx, tinman homolog |
|  | 1526 . . . 1519(91) |  |  |
| M00283 | 1863 . . . 1878(90) | Zeste | Zeste transvection gene product |
| M00046 | 1113 . . . 1105(90) | GCR1 | GCR1 |
| M00353 | 1069 . . . 1079(90) | Dof2 | Dof2 - single zinc finger transcription factor |
|  | 1951 . . . 1941(90) |  |  |
| M00263 | 985 . . . 994(90) | StuAp | Aspergillus Stunted protein |
| M00051 | 448 . . . 457(90) | NF-kappaB | NF-kappaB (p50) |
| M00350 | 1200 . . . 1191(90) | GATA-3 | GATA-binding factor 3 |
| M00276 | 1851 . . . 1860(90) | Mat1-Mc | M-box interacting with Mat1-Mc |
| M00075 | 1936 . . . 1945(90) | GATA-1 | GATA-binding factor 1 |
|  | 442 . . . 451(90) |  |  |
| M00355 | 279 . . . 269(90) | PBF | PBF (MPBF) |
|  | 1897 . . . 1887(90) |  |  |
| M00352 | 1775 . . . 1785(90) | Dof1 | Dof1/MNB1a - single zinc finger transcription factor |
| M00294 | 1670 . . . 1658(90) | HFH-8 | HNF-3/Fkh Homolog-8 |
| M00131 | 1762 . . . 1748(90) | HNF-3beta | Hepatocyte Nuclear Factor 3beta |
| M00137 | 1320 . . . 1332(90) | Oct-1 | octamer factor 1 |
| M00054 | 448 . . . 457(90) | NF-kappaB | NF-kappaB |

TABLE 10

(SEQ ID No.8)
Nucleotide sequence of coding region of human DUB7 (hDUB7)

ATGACCATAGTTGACAAAGCTTCTGAATCTTCAGACCCATCAGCCTATCAGAATC

AGCCTGGCAGCTCCGAGGCAGTCTCACCTGGAGACATGGATGCAGGTTCTGCCAG

CTGGGGTGCTGTGTCTTCATTGAATGATGTGTCAAATCACACACTTTCTTTAGGAC

CAGTACCTGGTGCTGTAGTTTATTCGAGTTCATCTGTACCTGATAAATCAAAACCA

TCACCACAAAAGGATCAAGCCCTAGGTGATGGCATCGCTCCTCCACAGAAAGTTC

TTTTCCCATCTGAGAAGATTTGTCTTAAGTGGCAACAAACTCATAGAGTTGGAGCT

GGGCTCCAGAATTTGGGCAATACCTGTTTTGCCAATGCAGCACTGCAGTGTTTAA

CCTACACACCACCTCTTGCCAATTACATGCTATCACATGAACACTCCAAAACATGT

CATGCAGAAGGCTTTTGTATGATGTGTACAATGCAAGCACATATTACCCAGGCAC

TCAGTAATCCTGGGGACGTTATTAAACCAATGTTTGTCATCAATGAGATGCGGCG

TATAGCTAGGCACTTCCGTTTTGGAAACCAAGAAGATGCCCATGAATTCCTTCAA

TACACTGTTGATGCTATGCAGAAAGCATGCTTGAATGGCAGCAATAAATTAGACA

GACACACCCAGGCCACCACTCTTGTTTGTCAGATATTTGGAGGATACCTAAGATC

TAGAGTCAAATGTTTAAATTGCAAGGGCGTTTCAGATACTTTTGATCCATATCTTG

ATATAACATTGGAGATAAAGGCTGCTCAGAGTGTCAACAAGGCATTGGAGCAGTT

TGTGAAGCCGGAACAGCTTGATGGAGAAAACTCGTACAAGTGCAGCAAGTGTAA

AAAGATGGTTCCAGCTTCAAAGAGGTTCACTATCCATAGATCCTCTAATGTTCTTA

CACTTTCTCTGAAACGTTTTGCAAATTTTACCGGTGGAAAAATTGCTAAGGATGTG

AAATACCCTGAGTATCTTGATATTCGGCCATATATGTCTCAACCCAACGGAGAGC

CAATTGTCTACGTCTTGTATGCAGTGCTGGTCCACACTGGTTTTAATTGCCATGCT

GGCCATTACTTCTGCTACATAAAAGCTAGCAATGGCCTCTGGTATCAAATGAATG

ACTCCATTGTATCTACCAGTGATATTAGATCGGTACTCAGCCAACAAGCCTATGTG

TABLE 10-continued

Nucleotide sequence of coding region of human DUB7 (hDUB7) (SEQ ID No.8)

CTCTTTTATATCAGGTCCCATGATGTGAAAAATGGAGGTGAACTTACTCATCCCAC

CCATAGCCCCGGCCAGTCCTCTCCCCGCCCCGTCATCAGTCAGCGGGTTGTCACCA

ACAAACAGGCTGCGCCAGGCTTTATCGGACCACAGCTTCCCTCTCACATGATAAA

GAATCCACCTCACTTAAATGGGACTGGACCATTGAAAGACACGCCAAGCAGTTCC

ATGTCGAGTCCTAACGGGAATTCCAGTGTCAACAGGGCTAGTCCTGTTAATGCTT

CAGCTTCTGTCCAAAACTGGTCAGTTAATAGGTCCTCAGTGATCCCAGAACATCCT

AAGAAACAAAAAATTACAATCAGTATTCACAACAAGTTGCCTGTTCGCCAGTGTC

AGTCTCAACCTAACCTTCATAGTAATTCTTTGGAGAACCCTACCAAGCCCGTTCCC

TCTTCTACCATTACCAATTCTGCAGTACAGTCTACCTCGAACGCATCTACGATGTC

AGTTTCTAGTAAAGTAACAAAACCGATCCCCCGCAGTGAATCCTGCTCCCAGCCC

GTGATGAATGGCAAATCCAAGCTGAACTCCAGCGTGCTGGTGCCCTATGGCGCCG

AGTCCTCTGAGGACTCTGACGAGGAGTCAAAGGGGCTGGGCAAGGAGAATGGGA

TTGGTACGATTGTGAGCTCCCACTCTCCCGGCCAAGATGCCGAAGATGAGGAGGC

CACTCCGCACGAGCTTCAAGAACCCATGACCCTAAACGGTGCTAATAGTGCAGAC

AGCGACAGTGACCCGAAAGAAAACGGCCTAGCGCCTGATGGTGCCAGCTGCCAA

GGCCAGCCTGCCCTGCACTCAGAAAATCCCTTTGCTAAGGCAAACGGTCTTCCTG

GAAAGTTGATGCCTGCTCCTTTGCTGTCTCTCCCAGAAGACAAAATCTTAGAGAC

CTTCAGGCTTAGCAACAAACTGAAAGGCTCGACGGATGAAATGAGTGCACCTGG

AGCAGAGAGGGGCCCTCCCGAGGACCGCGACGCCGAGCCTCAGCCTGGCAGCCC

CGCCGCCGAATCCCTGGAGGAGCCAGATGCGGCCGCCGGCCTCAGCAGCACCAA

GAAGGCTCCGCCGCCCCGCGATCCCGGCACCCCCGCTACCAAAGAAGGCGCCTGG

GAGGCCATGGCCGTCGCCCCCGAGGAGCCTCCGCCCAGCGCCGGCGAGGACATC

GTGGGGGACACAGCACCCCCTGACCTGTGTGATCCCGGGAGCTTAACAGGCGATG

CGAGCCCGTTGTCCCAGGACGCAAAGGGGATGATCGCGGAGGGCCCGCGGGACT

CGGCGTTGGCGGAAGCCCCGGAAGGGTTGAGTCCGGCTCCGCCTGCGCGGTCGGA

GGAGCCCTGCGAGCAGCCACTCCTTGTTCACCCCAGCGGGGACCACGCCCGGGAC

GCTCAGGACCCATCCCAGAGCTTGGGCGCACCCGAGGCCGCAGAGCGGCCGCCA

GCTCCTGTGCTGGACATGGCCCCGGCCGGTCACCCGGAAGGGGACGCTGAGCCTA

GCCCCGGCGAGAGGGTCGAGGACGCCGCGGCGCCGAAAGCCCCAGGCCCTTCCC

CAGCGAAGGAGAAAATCGGCAGCCTCAGAAAGGTGGACCGAGGCCACTACCGCA

GCCGGAGAGAGCGCTCGTCCAGCGGGGAGCCCGCCAGAGAGAGCAGGAGCAAG

ACTGAGGGCCACCGTCACCGGCGGCGCCGCACCTGCCCCGGGAGCGCGACCGC

CAGGACCGCCACGCCCCGGAGCACCACCCCGGCCACGGCGACAGGCTCAGCCCT

GGCGAGCGCCGCTCTCTGGGCAGGTGCAGTCACCACCACTCCCGACACCGGAGCG

GGGTGGAGCTGGACTGGGTCAGACACCACTACACCGAGGGCGAGCGTGGCTGGG

GCCGGGAGAAGTTCTACCCCGACAGGCCGCGCTGGGACAGGTGCCGGTACTACC

ATGACAGGTACGCCCTGTACGCTGCCCGGGACTGGAAGCCCTTCCACGGCGGCCG

CGAGCACGAGCGGGCCGGGCTGCACGAGCGGCCGCACAAGGACCACAACCGGGG

TABLE 10-continued (SEQ ID No.8)
Nucleotide sequence of coding region of human DUB7 (hDUB7)

CCGTAGGGGCTGCGAGCCGGCCCGGGAGAGGGAGCGGCACCGCCCCAGCAGCCC

CCGCGCAGGCGCGCCCCACGCCCTCGCCCCGCACCCCGACCGCTTCTCCCACGAC

AGAACTGCACTTGTAGCCGGAGACAACTGTAACCTCTCTGATCGGTTTCACGAAC

ACGAAAATGGAAAGTCCCGGAAACGGAGACACGACAGTGTGGAGAACAGTGACA

GTCATGTTGAAAAGAAAGCCCGGAGGAGCGAACAGAAGGATCCTCTAGAAGAGC

CTAAAGCAAAGAAGCACAAAAAATCAAAGAAGAAAAAGAAATCCAAAGACAAA

CACCGAGACCGCGACTCCAGGCATCAGCAGGACTCAGACCTCTCAGCAGCGTGCT

CTGACGCTGACCTCCACAGACACAAAAAAAAGAAGAAGAAAAAGAAGAGACATT

CAAGAAAATCAGAGGACTTTGTTAAAGATTCAGAACTGCACTTACCCAGGGTCAC

CAGCTTGGAGACTGTCGCCCAGTTCCGGAGAGCCCAGGGTGGCTTTCCTCTCTCTG

GTGGCCCGCCTCTGGAAGGCGTCGGACCTTTCCGTGAGAAAACGAAACACTTACG

GATGGAAAGCAGGGATGACAGGTGTCGTCTCTTTGAGTATGGCCAGGGTGATTGA

TABLE 11

SEQ ID No.9)
Deduced amino acid sequence of coding region of hDUB7
C-terminal potential nuclear localization (as well
as targeting) sequences are underlined.

MTIVDKASESSDPSAYQNQPGSSEAVSPGDMDAGSASWGAVSSLNDVSNHTLSLGPV

PGAVVYSSSSVPDKSKPSPQKDQALGDGIAPPQKVLFPSEKICLKWQQTHRVGAGLQ

NLGNTCFANAALQCLTYTPPLANYMLSHEHSKTCHAEGFCMMCTMQAHITQALSNP

GDVIKPMFVINEMRRIARHFRFGNQEDAHEFLQYTVDAMQKACLNGSNKLDRHTQA

TTLVCQIFGGYLRSRVKCLNCKGVSDTFDPYLDITLEIKAAQSVNKALEQFVKPEQLD

GENSYKCSKCKKMVPASKRFTIHRSSNVLTLSLKRFANFTGGKIAKDVKYPEYLDIRP

YMSQPNGEPIVYVLYAVLVHTGFNCHAGHYFCYIKASNGLWYQMNDSIVSTSDIRSV

LSQQAYVLFYIRSHDVKNGGELTHPTHSPGQSSPRPVISQRVVTNKQAAPGFIGPQLPS

HMIKNPPHLNGTGPLKDTPSSSMSSPNGNSSVNRASPVNASASVQNWSVNRSSVIPEH

PKKQKITISIHNKLPVRQCQSQPNLHSNSLENPTKPVPSSTITNSAVQSTSNASTMSVSS

KVTKPIPRSESCSQPVMNGKSKLNSSVLVPYGAESSEDSDEESKGLGKENGIGTIVSSH

SPGQDAEDEEATPHELQEPMTLNGANSADSDSDPKENGLAPDGASCQGQPALHSENP

FAKANGLPGKLMPAPLLSLPEDKILETFRLSNKLKGSTDEMSAPGAERGPPEDRDAEP

QPGSPAAESLEEPDAAAGLSSTKKAPPPRDPGTPATKEGAWEAMAVAPEEPPPSAGE

DIVGDTAPPDLCDPGSLTGDASPLSQDAKGMIAEGPRDSALAEAPEGLSPAPPARSEEP

CEQPLLVHPSGDHARDAQDPSQSLGAPEAAERPPAPVLDMAPAGHPEGDAEPSPGER

VEDAAAPKAPGPSPAKLEKIGSLRKVDRGHYRSRRERSSSGEPARESRSKTEGHRHRRR

RTCPRERDRQDRHAPEHHPGHGDRLSPGERRSLGRCSHHHSRHRSGVELDWVRHHY

TEGERGWGREKFYPDRPRWDRCRYYHDRYALYAARDWKPFHGGREHERAGLHERP

HKDHNRGRRGCEPARERERHRPSSPRAGAPHALAPHPDRFSHDRTALVAGDNCNLSD

RFHEHENGKSRKRRHDSVENSDSHVEKKARRSEQKDPLEEP<u>KAKKHKKSKKKKKSK</u>

TABLE 11-continued

SEQ ID No.9)
Deduced amino acid sequence of coding region of hDUB7
C-terminal potential nuclear localization (as well
as targeting) sequences are underlined.

DKHRDRDSRHQQDSDLSAACSDADLHRHKKKKKKKKRHSRKSEDFVKDSELHLPRV

TSLETVAQFRRAQGGFPLSGGPPLEGVGPFREKTKHLRMESRDDRCRLFEYGQGD

TABLE 12

SEQ ID No.10)
Putative promoter sequence of hDUB7 (2 Kb sequence upstream
of initiation AUG)

GTAAAGTCTAAACTGAGAAGTGGAAGTGTGAACTGGCTGGAGGTGGAAGGTTGG

AAAAGAGTCGGAGAAAAGAACAGCATGTGCAGAGCCCAGAGACAGCAGGGACA

AAAGAAAAAAAAACAAGACTTCAGCATGGTGGGAACGTGACGGAGAGGGTGTTT

GGCGAGGTTATTAGGTCAGACAATGTGAAGTCCAGACATTAAGATGTTGTGCTGT

GGGCAGTTGGGCCACTCCTGAAAGGTGTTCTTTCTTCCTTTCCTTTTCTTTCTTTCT

TTTCTTGAGGCAGAGTCTCTCTATGTCAGTCTGGAGTGCAGTGGCATGATCTCGGC

TCACTGCAATCTCTGCCTTCCAGGTTCAAGCAATTTTCCTTGCCTCAGCCTCCCAA

GTAGCTGGGAATACAGGCGTGCGCCACCATGCCTGGTTAATTTTTTATTTTTAGT

AGAGATGGGGTTTCCCCATGTTGGCCAGGCTGGTCTCGAACTCCTGGACTCAAGT

GATCCACCCACTTTGGCCTCCCAAAGTGCTGGGATTACAGGGGTGTGAGCCACTG

CGCCCCGCCCGGCCTTTTTTTTTTTTTTTTGAGACTTAATCTTGCTCTGTCACCA

AGGCTGGATATCAGTGGCACGGTTTTGGCTCTCTGCAACTTCTGTCTCCCAGGTTC

AAGCGATTTTCCTGACTCAGCCTCCCAAGTAGTTGAGATTACAGGTACGTGCCAC

CACGCCCGGCTAATTTTTGTATTTTTAGTAGAGATGAGGTTTCACTATGTTGGCCA

GACTGGTCTCAAACGCCTGACCTCAGGTGATTCACCTGCCTCGGCCTCCCAAAAT

GCTGGGATTACAGGTGTGCACCACCATGCCTGGGTAATTTTTGTTTTTCGTAGAGA

CAGGGTCTCACCATGTTGGCCAGGCTGGTCTCAAACTCCTGACCTCAAGCGATCT

GCCCACCTTGGCCTCCCAAGGTGCTGCAATTATAGGCATGAGCCACCGCGCCCGG

CCTCCTGAAAGGTTTTCTACATAGGAGTGGCATGTCTAGATGTGGCTACTGTTGGG

CGATTTTAGAAATATCCCTAAAAGCCTTCTGTTGACAGGGTGGCATAACCAGAAG

GAAGCCTGGCTGGGAACGCTGGACCTGGCTCTCAGTCCCAGTTGCTGACTGGTTG

CTTCATTTTATAGGCCCTGGGGATTCTGTCTGATCTCTCATACGTTCTTTATAAAA

ATTAAGTTAATGTATGTCCAGCAGTTGATGCAATGCCCAGTACATAGAAAATGCT

CAATTAGTGGTAGCCCTAATATTTTAAAATAGGACTCAGAAAGAAAATTATAATC

AAGTCCTTTCATAACAGATATTTGTGTTTGAGTTTGATATCAGTAATGGCTTACGG

GTTTTATTTAAAAAGTCATACATTCCATATAAATGAGCCTCTTCAGAAAAATGGTT

TTAAAGGTGAGATCTCTATAATTATAATTTTAAAAAATATAATGTATTTCACTTGG

TGCCATTTGCACTTTAAGCACAAAATTAAGTCTAGATTTTTTCTGTGTAGTTGATG

CTTTTCTCTGAGGAATTATACTCAAATTGAAGATGTAGTCAAATGTATTACTGTGT

ATAATTTTTCTAGTTTTAAGCAGTATAGAAGGAAAATATAGGTACTTAGTAAATA

TABLE 12-continued

Putative promoter sequence of hDUB7 (2 Kb sequence upstream of initiation AUG) (SEQ ID No.10)

AACAGAACTGAGAATTGAAATGTCCAATTATAAACTGAAATGCCAGACTTTTAGG

GGGCATGAAATGAAAATGAGAAGTTCTTTTAATCAAATACTTCACTGAAGATTTT

AAAATAAAGATTGTTGACATTCAGATTATCATGATGCTAAATGTCCCAAGGGGAT

TATTACAGAAATGTTAGAAAGTACTATTGTTTTTATATTTGAGTGATGTGTTTGAA

AATCACTTTAAAATGGCTGGAATGATCTTCCAAGATCTAACGGTAGGGTAAGGAG

ATTGCTTTTCTCACCTGATGAAACAAATACATACTTTTCATCTTTTGCAGAGTTGA

ACA<u>ATG</u>

TABLE 13

Nucleotide sequence of coding region of murine DUB7 (mDUB7) (SEQ ID No.11)

ATGACCATAGTTGACAAAACTGAACCTTCAGACCCATCAACCTGTCAGAACCAGC

CTGGCAGTTGTGAGGCGGTCTCACCTGAAGACATGGACACAGGCTCTGCCAGCTG

GGGCGCTGTGTCTTCAATAAGTGATGTCTCAAGTCACACACTTCCATTAGGGCCA

GTGCCTGGTGCTGTAGTTTATTCTAACTCGTCTGTACCTGAAAAATCAAAGCCATC

ACCACCAAAGGATCAAGTCCTAGGTGATGGCATTGCTCCTCCTCAAAAGGTCCTG

TTTCCATCTGAAAAGATTTGTCTTAAGTGGCAACAAAGTCATCGAGTTGGCGCTG

GGCTCCAGAATTTGGGCAACACCTGTTTTGCCAATGCCGCATTGCAGTGTCTGACT

TACACGCCACCCCTCGCCAATTACATGTTATCCCATGAACACTCCAAGACATGCC

ACGCAGAAGGATTTTGTATGATGTGCACGATGCAGACACACATTACCCAGGCACT

TAGCAACCCTGGGGATGTTATCAAGCCGATGTTCGTCATCAATGAAATGCGGCGT

ATAGCTAGACACTTCCGTTTTGGAAACCAAGAAGATGCCCATGAATTTCTTCAGT

ACACGGTCGATGCCATGCAGAAAGCATGTTTAAATGGCAGCAATAAATTAGACA

GACACACCCAGGCCACCACCCTGGTCTGCCAGATATTTGGAGGCTACCTAAGATC

CCGAGTTAAATGTTTAAATTGCAAGGGTGTTTCAGATACCTTTGATCCATATCTGG

ACATAACGTTGGAGATTAAGGCTGCACAGAGTGTTACCAAGGCGTTAGAGCAGTT

TGTGAAGCCAGAACAACTGGATGGAGAAAACTCCTACAAGTGCAGCAAGTGCAA

AAAAATGGTTCCAGCTTCAAAGAGATTCACAATCCATAGGTCCTCTAATGTTCTTA

CCATCTCACTGAAGCGCTTTGCCAACTTCACCGGTGGAAAGATTGCTAAGGATGT

GAAATATCCTGAGTACCTTGATATCCGGCCCTATATGTCTCAGCCCAATGGAGAG

CCAATTATTTATGTTTTGTATGCTGTGCTGGTGCACACTGGTTTTAATTGTCATGCT

GGCCACTACTTTTGCTACATCAAGGCTAGCAATGGCCTCTGGTATCAGATGAATG

ACTCCATCGTGTCCACCAGTGATATCAGAGCAGTGCTTAACCAGCAAGCTTACGT

GCTCTTTTATATCAGGTCCCATGATGTGAAAAATGGAGGGGAGTCTGCTCATCCT

GCCCATAGCCCCGGCCAATCCTCTCCCCGCCCAGGAGTCAGTCAGCGGGTAGTCA

ACAACAAGCAGGTGGCTCCAGGGTTTATTGGACCCCAGCTGCCTTCCCATGTGAT

GAAGAACACGCCACACTTGAATGGCACCACGCCAGTGAAAGACACACCAAGTAG

TABLE 13-continued

Nucleotide sequence of coding region of murine DUB7
(mDUB7) SEQ ID No.11)

TTCTGTGTCAAGCCCTAACGGAAACACCAGCGTCAATAGGGCCAGTCCTGCTACT

GCTTCGACTTCTGTGCAGAACTGGTCTGTTACCAGACCCTCAGTTATTCCAGATCA

CCCCAAGAAACAAAAAATCACCATCAGTATTCACAACAAGTTGCCTGCTCGCCAG

GGTCAGGCACCACTGAATAACAGCCTCCATGGCCCTTGTCTGGAGGCTCCTAGTA

AGGCGGCACCCTCCTCCACCATCACTAACCCTTCTGCAATACAGTCTACCTCGAAC

GTACCCACAACGTCGACTTCCCCCAGTGAGGCCTGTCCCAAGCCCATGGTGAACG

GCAAGGCTAAAGTGGGCGCCAGTGTGCTTGTCCCCTATGGGGCCGAGTCCTCAGA

AGAGTCTGATGAGGAGTCGAAGGGCCTGGCCAAGGAGAACGGTGTGGACATGAT

GGCCGGCACTCACTCCGATAGGCCAGAAGCTGCTGCAGATGACGGTGCTGAGGCT

TCCTCCCATGAGCTTCAAGAACCCGTCCTGCTAAATGGTGCTAATAGCGCAGACA

GTGACTCACAAGAGAACAGCCTGGCATTTGACAGTGCCAGCTGCCAGGTCCAGCC

CGAGCTACACAGAAAACCTCTTTTCCAAACTTAATGGTCTTCCTGGAAAGGTG

ACGCCTGCTCCTTTGCAGTCTGTTCCTGAAGACAGAATCCTTGAGACCTTCAAGCT

TACCAACCAGGCAAAGGGTCCAGCGGGTGAAGAGAGTTGGACTACGACAGGGGG

AAGCTCTCCAAAGGACCCTGTTTCACAGCTGGAGCCCATCAGTGATGAGCCCAGT

CCCCTTGAGATACCGGAGGCTGTCACCAATGGGAGCACACAGACCCCTTCCACCA

CATCACCCCTGGAGCCCACCATCAGCTGTACCAAAGAAGACTCGTCCGTTGTTGT

CTCAGCTGAACCTGTGGAGGGTTTGCCTTCCGTCCCTGCTCTTTGTAACAGCACTG

GTACTATCTTGGGGGATACCCCAGTGCCCGAATTGTGTGACCCTGGAGACTTGAC

TGCCAACCCGAGCCAGCCAACCGAAGCAGTGAAAGGTGATACAGCTGAGAAGGC

TCAGGACTCTGCCATGGCTGAAGTGGTGGAGAGGCTGAGCCCTGCTCCCTCAGTA

CTCACAGGTGACGGGTGTGAGCAGAAACTCTTACTTTACCTCAGCGCAGAGGGT

CAGAGGAGACAGAAGACTCTTCCAGAAGCTCGGCGGTCTCTGCTGACACGATGCC

CCCTAAGCCTGACAGGACCACCACCAGCTCCTGTGAAGGGGCTGCCGAGCAGGCT

GCTGGGGACAGAGGCGATGGAGGCCATGTGGGACCCAAAGCTCAGGAGCCTTCC

CCAGCCAAGGAAAAGATGAGCAGCCTCCGGAAAGTGGACCGAGGACACTATCGG

AGCCGGAGAGAGCGCTCCTCCAGTGGGGAGCACGTGAGGGACAGCAGGCCCCGG

CCGGAGGACCATCACCATAAGAAGCGGCACTGCTACAGCCGAGAGCGGCCCAAG

CAGGACCGACACCCTACTAATTCATACTGCAATGGGGCCAGCACTTGGGCCACG

GGGACAGAGCCAGCCCTGAGCGCCGCTCCCTGAGCAGGTATAGTCACCACCACTC

ACGGATTAGGAGTGGCCTGGAGCAGGACTGGAGCCGGTACCACCATTTGGAAAA

TGAGCATGCTTGGGTCAGGGAGAGATTCTACCAGGACAAGCTGCGGTGGGACAA

GTGCAGGTATTACCACGACAGGTACACGCCCCTATACACGGCCCGGGACGCCCGA

GAATGGCGGCCTCTGCATGGTCGTGAGCATGACCGCCTTGTCCAGTCTGGACGGC

CATACAAGGACAGCTACTGGGGCCGCAAGGGCTGGGAGCTGCAATCCCGGGGGA

AGGAACGGCCCCACTTCAACAGCCCCCGAGAGGCCCCTAGCCTTGCTGTGCCCCT

CGAGAGACATCTCCAAGAGAAGGCTGCGCTGAGTGTGCAGGACAGCAGCCACAG

TCTCCCTGAGCGCTTTCATGAACACAAAAGTGTCAAGTCGAGGAAGCGGAGGTAT

TABLE 13-continued

Nucleotide sequence of coding region of murine DUB7 (mDUB7) (SEQ ID No.11)

```
GAGACTCTAGAAAATAATGATGGCCGTCTAGAAAAGAAAGTCCACAAAAGCCTG

GAGAAGGACACGCTAGAGGAGCCAAGGGTGAAGAAGCACAAAAAGTCTAAAAA

GAAAAAGAAGTCCAAAGATAAACACCGGGATCGAGAAAGCAGGCACCAGCAGG

AGTCTGATTTTTCAGGAGCATACTCTGATGCTGACCTCCATAGACACCGGAAGAA

AAAGAAGAAAAAGAAAAGGCATTCCAGGAAGTCGGAGGACTTTATAAAGGATGT

TGAGATGCGTTTACCGAAGCTCTCCAGCTACGAGGCCGGCGGCCATTTCCGGAGA

ACAGAGGGCAGCTTTCTCCTGGCTGATGGTCTGCCTGTGGAAGACAGCGGCCCTT

TCCGGGAGAAAACGAAGCATTTAAGGATGGAAAGCCGGCCTGACAGATGCCGTC

TGTCGGAGTATGGCCAGGATTCAACATTTTGA
```

TABLE 14

Deduced amino acid sequence of coding region of mDUB7 C-terminal potential nuclear localization (as well as targeting) sequences are underlined. (SEQ ID No.12)

```
MTIVDKTEPSDPSTCQNQPGSCEAVSPEDMDTGSASWGAVSSISDVSSHTLPLGPVPG

AVVYSNSSVPEKSKPSPPKDQVLGDGIAPPQKVLFPSEKICLKWQQSHRVGAGLQNL

GNTCFANAALQCLTYTPPLANYMLSHEHSKTCHAEGFCMMCTMQTHITQALSNPGD

VIKPMFVINEMRRIARHFRFGNQEDAHEFLQYTVDAMQKACLNGSNKLDRHTQATT

LVCQIFGGYLRSRVKCLNCKGVSDTFDPYLDITLEIKAAQSVTKALEQFVKPEQLDGE

NSYKCSKCKKMVPASKRFTIHRSSNVLTISLKRFANFTGGKIAKDVKYPEYLDIRPYM

SQPNGEPIIYVLYAVLVHTGFNCHAGHYFCYIKASNGLWYQMNDSIVSTSDIRAVLNQ

QAYVLFYIRSHDVKNGGESAHPAHSPGQSSPRPGVSQRVVNNKQVAPGFIGPQLPSH

VMKNTPHLNGTTPVKDTPSSSVSSPNGNTSVRASPATASTSVQNWSVTRPSVIPDHP

KKQKITISIHNKLPARQGQAPLNNSLHGPCLEAPSKAAPSSTITNPSAIQSTSNVPTTSTS

PSEACPKPMVNGKAKVGASVLVPYGAESSEESDEESKGLAKENGVDMMAGTHSDRP

EAAADDGAEASSHELQEPVLLNGANSADSDSQENSLAFDSASCQVQPELHTENLFSK

LNGLPGKVTPAPLQSVPEDRILETFKLTNQAKGPAGEESWTTTGGSSPKDPVSQLEPIS

DEPSPLEIPEAVTNGSTQTPSTTSPLEPTISCTKEDSSVVVSAEPVEGLPSVPALCNSTGT

ILGDTPVPELCDPGDLTANPSQPTEAVKGDTAEKAQDSAMAEVVERLSPAPSVLTGD

GCEQKLLLYLSAEGSEETEDSSRSSAVSADTMPPKPDRTTTSSCEGAAEQAAGDRGD

GGHVGPKAQEPSPAKEKMSSLRKVDRGHYRSRRERSSSGEHVRDSRPRPEDHHHKK

RHCYSRERPKQDRHPTNSYCNGGQHLGHGDRASPERRSLSRYSHHHSRIRSGLEQDW

SRYHHLENEHAWVRERFYQDKLRWDKCRYYHDRYTPLYTARDARFWRPLHGREHD

RLVQSGRPYKDSYWGRKGWELQSRGKERPHFNSPREAPSLAVPLERHLQEKAALSV

QDSSHSLPERFHEHKSVKSRKRRYETLENNDGRLEKKVHKSLEKDTLEEPRVKKHKK
```

TABLE 14-continued

Deduced amino acid sequence of coding region of mDUB7
SEQ ID No.12)
C-terminal potential nuclear
localization (as well as targeting) sequences are underlined.

<u>SKKKKKSKDKHR</u>DRESRHQQESDFSGAYSDADL<u>HRHRKKKKKKKRHSRK</u>SEDFIKD

VEMRLPKLSSYEAGGHFRRTEGSFLLADGLPVEDSGPFREKTRHLRMESRPDRCRLSE

YGQDSTF

TABLE 15

Nucleotide sequence alignment of hDUB7 SEQ ID No.8)
and mDUB7 SEQ ID No.11)

```
HDUB7  ATGACCATAGTTGACAAAGCTTCTGAATCTTCAGACCCATCAGCCTATCAGAATCAGCCT  60
MDUB7  ATGACCATAGTTGACAAAA---CTGAACCTTCAGACCCATCAACCTGTCAGAACCAGCCT  57
       ******************    ***** ************** *** ****** ******

HDUB7  GGCAGCTCCGAGGCAGTCTCACCTGGAGACATGGATGCAGGTTCTGCCAGCTGGGGTGCT  120
MDUB7  GGCAGTTGTGAGGCGGTCTCACCTGAAGACATGGACACAGGCTCTGCCAGCTGGGGCGCT  117
       ***** * ***** ***********  ********   **** ************ ***

EDUB7  GTGTCTTCATTGAATGATGTGTCAAATCACACACTTTCTTTAGGACCAGTACCTGGTGCT  180
MDUB7  GTGTCTTCAATAAGTGATGTCTCAAGTCACACACTTCCATTAGGGCCAGTGCCTGGTGCT  177
       ********* *  ******* **** ********** *  ****  ***** ********

HDUB7  GTAGTTTATTCGAGTTCATCTGTACCTGATAAATCAAAACCATCACCACAAAAGGATCAA  240
MDUB7  GTAGTTTATTCTAACTCGTCTGTACCTGAAAAATCAAAGCCATCACCACCAAAGGATCAA  237
       ***********    **  ********** ******** ********** **********

HDUB7  GCCCTAGGTGATGGCATCGCTCCTCCACAGAAAGTTCTTTTCCCATCTGAGAAGATTTGT  300
MDUB7  GTCCTAGGTGATGGCATTGCTCCTCCTCAAAAGGTCCTGTTTCCATCTGAAAAGATTTGT  297
       * *************** ******** ** ** ** ** ** ********* ********

HDUB7  CTTAAGTGGCAACAAACTCATAGAGTTGGAGCTGGGCTCCAGAATTTGGGCAATACCTGT  360
MDUB7  CTTAAGTGGCAACAAAGTCATCGAGTTGGCGCTGGGCTCCAGAATTTGGGCAACACCTGT  357
       ****************  ****  ****** * ****************** ******

HDUB7  TTTGCCAATGCAGCACTGCAGTGTTTAACCTACACACCACCTCTTGCCAATTACATGCTA  420
MDUB7  TTTGCCAATGCCGCATTGCAGTGTCTGACTTACACGCCACCCCTCGCCAATTACATGTTA  417
       *********** *** ********  *  ****** ***** ** ************ **

HDUB7  TCACATGAACACTCCAAAACATGTCATGCAGAAGGCTTTTGTATGATGTGTACAATGCAA  480
MDUB7  TCCCATGAACACTCCAAGACATGCCACGCAGAAGGATTTTGTATGATGTGCACGATGCAG  477
       ** **************  **** **  ****** *************  ** ****

HDUB7  GCACATATTACCCAGGCACTCAGTAATCCTGGGGACGTTATTAAACCAATGTTTGTCATC  540
MDUB7  ACACACATTACCCAGGCACTTAGCAACCCTGGGGATGTTATCAAGCCGATGTTCGTCATC  537
       ****  ************** ** ** ******** ***** ** ** ***** ******

HDUB7  AATGAGATGCGGCGTATAGCTAGGCACTTCCGTTTTGGAAACCAAGAAGATGCCCATGAA  600
MDUB7  AATGAAATGCGGCGTATAGCTAGACACTTCCGTTTTGGAAACCAAGAAGATGCCCATGAA  597
       ***** ***************** ************************************

HDUB7  TTCCTTCAATACACTGTTGATGCTATGCAGAAAGCATGCTTGAATGGCAGCAATAAATTA  660
MDUB7  TTTCTTCAGTACACGGTCGATGCCATGCAGAAAGCATGTTTAAATGGCAGCAATAAATTA  657
       ** ***** ***** ** ***** ************* ** ******************

HDUB7  GACAGACACACCCAGGCCACCACTCTTGTTTGTCAGATATTTGGAGGATACCTAAGATCT  720
MDUB7  GACAGACACACCCAGGCCACCACCCTGGTCTGCCAGATATTTGGAGGCTACCTAAGATCC  717
       *********************** ** ** ** ************** **********

HDUB7  AGAGTCAAATGTTTAAATTGCAAGGGCGTTTCAGATACTTTTGATCCATATCTTGATATA  780
MDUB7  CGAGTTAAATGTTTAAATTGCAAGGGTGTTTCAGATACCTTTGATCCATATCTGGACATA  777
       *********************** ************ *************  ** ***

HDUB7  ACATTGGAGATAAAGGCTGCTCAGAGTGTCAACAAGGCATTGGAGCAGTTTGTGAAGCCG  840
MDUB7  ACGTTGGAGATTAAGGCTGCACAGAGTGTTACCAAGGCGTTAGAGCAGTTTGTGAAGCCA  837
       ** ******** ******** ******** ** ***** ** **************** *

HDUB7  GAACAGCTTGATGGAGAAAACTCGTACAAGTGCAGCAAGTGTAAAAAGATGGTTCCAGCT  900
MDUB7  GAACAACTGGATGGAGAAAACTCCTACAAGTGCAGCAAGTGCAAAAAAATGGTTCCAGCT  897
       ***** ** **************  ***************** ***** **********
```

TABLE 15-continued

Nucleotide sequence alignment of hDUB7 SEQ ID No.8)
and mDUB7 SEQ ID No.11)

```
HDUB7  TCAAAGAGGTTCACTATCCATAGATCCTCTAATGTTCTTACACTTTCTCTGAAACGTTTT  960
MDUB7  TCAAAGAGATTCACAATCCATAGGTCCTCTAATGTTCTTACCATCTCACTGAAGCGCTTT  957
       ******* ***** ******** *****************  * ** ***** ** ***

HDUB7  GCAAATTTTACCGGTGGAAAAATTGCTAAGGATGTGAAATACCCTGAGTATCTTGATATT  1020
MDUB7  GCCAACTTCACCGGTGGAAAGATTGCTAAGGATGTGAAATATCCTGAGTACCTTGATATC  1017
       ** ** ** *********** ******************** ******** ********

HDUB7  CGGCCATATATGTCTCAACCCAACGGAGAGCCAATTGTCTACGTCTTGTATGCAGTGCTG  1080
MDUB7  CGGCCCTATATGTCTCAGCCCAATGGAGAGCCAATTATTTATGTTTTGTATGCTGTGCTG  1077
       ***** *********** ***** *********** ** ** ******** ******

HDUB7  GTCCACACTGGTTTTAATTGCCATGCTGGCCATTACTTCTGCTACATAAAAGCTAGCAAT  1140
MDUB7  GTGCACACTGGTTTTAATTGTCATGCTGGCCACTACTTTTGCTACATCAAGGCTAGCAAT  1137
       ** ***************** *********** ***** ******* ** *********

HDUB7  GGCCTCTGGTATCAAATGAATGACTCCATTGTATCTACCAGTGATATTAGATCGGTACTC  1200
MDUB7  GGCCTCTGGTATCAGATGAATGACTCCATCGTGTCCACCAGTGATATCAGAGCAGTGCTT  1197
       ************** ************** ** ** ********** *** * ** **

HDUB7  AGCCAACAAGCCTATGTGCTCTTTTATATCAGGTCCCATGATGTGAAAAATGGAGGTGAA  1260
MDUB7  AACCAGCAAGCTTACGTGCTCTTTTATATCAGGTCCCATGATGTGAAAAATGGAGGGGAG  1257
       * *** ***** ** *****************************************  *

HDUB7  CTTACTCATCCCACCCATAGCCCCGGCCAGTCCTCTCCCCGCCCCGTCATCAGTCAGCGG  1320
MDUB7  TCTGCTCATCCTGCCCATAGCCCCGGCCAATCCTCTCCCCGCCCAGGAGTCAGTCAGCGG  1317
        * ******* ***************** **************  *  **********

HDUB7  GTTGTCACCAACAAACAGGCTGCGCCAGGCTTTATCGGACCACAGCTTCCCTCTCACATG  1380
MDUB7  GTAGTCAACAACAAGCAGGTGGCTCCAGGGTTTATTGGACCCCAGCTGCCTTCCCATGTG  1377
       ** **** ****** **** ****  ** ***** ***** ***** **  **  **

HDUB7  ATAAAGAATCCACCTCACTTAAATGGGACTGGACCATTGAAAGACACGCCAAGCAGTTCC  1440
MDUB7  ATGAAGAACACGCCACACTTGAATGGCACCACGCCAGTGAAAGACACACCAAGTAGTTCT  1437
       ** *****  * ** ***** ***** ** **    ********** ***** *****

HDUB7  ATGTCGAGTCCTAACGGGAATTCCAGTGTCAACAGGGCTAGTCCTGTTAATGCTTCAGCT  1500
MDUB7  GTGTCAAGCCCTAACGGAAACACCAGCGTCAATAGGGCCAGTCCTGCTACTGCTTCGACT  1497
        **** ** ******** **  **** ***** ***** ******* ** ****** **

HDUB7  TCTGTCCAAAACTGGTCAGTTAATAGGTCCTCAGTGATCCCAGAACATCCTAAGAAACAA  1560
MDUB7  TCTGTGCAGAACTGGTCTGTTACCAGACCCTCAGTTATTCCAGATCACCCCAAGAAACAA  1557
       ***** ** ******** ****   ** ******* ** ***** ** ** *********

HDUB7  AAAATTACAATCAGTATTCACAACAAGTTGCCTGTTCGCCAGTGTCAGTCTCAACCTAA-  1619
MDUB7  AAAATCACCATCAGTATTCACAACAAGTTGCCTGCTCGCCAGGGTCAGGCACCACTGAAT  1617
       ***** ** ************************ ******* ***** *  * ** **

HDUB7  -----CCTTCATAGTAATTCTTTGGAGAACCCTACCAAGCCCGTTCCCTCTTCTACCATT  1674
MDUB7  AACAGCCTCCATGGCCCTTGTCTGGAGGCTCCTAGTAAGGCGGCACCCTCCTCCACCATC  1677
            *** ***  *  ** *****  ****  *** ***** ** *****

HDUB7  ACCAA---TTCTGCAGTACAGTCTACCTCGAACGCATCTACGATGTCAGTTTCTAGTAAA  1731
MDUB7  ACTAACCCTTCTGCAATACAGTCTACCTCGAACGTACCCACACGTCGACTTC-------  1730
       ** **   ******* ******************  *  * ** *** ***

HDUB7  GTAACAAAACCGATCCCCCGCAGTGAATCCTGCTCCCAGCCCGTGATGAATGGCAAATCC  1791
MDUB7  ----------------CCCCAGTGAGGCCTGTCCCAAGCCCATGGTGAACGGCAAGGCT  1773
                       ** ****** **** **** **** ** **** ***** *

HDUB7  AAGCTGAACTCCAGCGTGCTGGTGCCCTATGGCGCCGAGTCCTCTGAGGACTCTGACGAG  1851
MDUB7  AAAGTGGGCGCCAGTGTGCTTGTCCCCTATGGGGCCGAGTCCTCAGAAGAGTCTGATGAG  1833
       ** ** * **** ******  ** ******** *********** ** ** ***** ***

HDUB7  GAGTCAAAGGGGCTGGGCAAGGAGAATGGGATTGGTACGATTGTGAGCTCCCACTCTCCC  1911
MDUB7  GAGTCGAAGGGCCTGGCCAAGGAGAACGGTGTGGACATGATGGCCGGCACTCACTCCGAT  1893
       ***** *****  *****  ***** ** *  * *   **  *  **  *  * *****

HDUB7  GGCCAAGA---TGCCGAAGATGAGG------AGGCCACTCCGCACGAGCTTCAAGAACCC  1962
MDUB7  AGGCCAGAAGCTGCTGCAGATGACGGTGCTGAGGCTTCCTCCCATGAGCTTCAAGAACCC  1953
        * ***  *   *** * *****  *      **** * * ** ****************

HDUB7  ATGACCCTAAACGGTGCTAATAGTGCAGACAGCGACAGTGACCCGAAAGAAAACGGCCTA  2022
MDUB7  GTCCTGCTAAATGGTGCTAATAGCGCAGA------CAGTGACTCACAAGAGAACAGCCTG  2007
        *  ***** ************ *****      ******* *  *  *** *** ***
```

TABLE 15-continued

Nucleotide sequence alignment of hDUB7 SEQ ID No.8)
and mDUB7 SEQ ID No.11)

```
HDUB7  GCGCCTGATGGTGCCAGCTGCCAAGGCCAGCCTGCCCTGCACTCAGAAAATCCCTTTGCT  2082
MDUB7  GCATTTGACAGTGCCAGCTGCCAGGTCCAGCCCGAGCTACACACAGAAAACCTCTTTTCC  2067
       **  ***  ************  ******  *  **  ***  *******  *  ****  *

HDUB7  AAGGCAAACGGTCTTCCTGGAAAGTTGATGCCTGCTCCTTTGCTGTCTCTCCCAGAAGAC  2142
MDUB7  AAACTTAATGGTCTTCCTGGAAAGGTGACGCCTGCTCCTTTGCAGTCTGTTCCTGAAGAC  2127
       **    **  ***************  ***  *************  ****  *  **  ******

HDUB7  AAAATCTTAGAGACCTTCAGGCTTAGCAACAAACTGAAAGGCTCGACGGATGAAATGAGT  2202
MDUB7  AGAATCCTTGAGACCTTCAAGCTTACCAACCAGGCAAAGGGTCCAGCGGGTGAAGAGAGT  2187
       *  ****  *  **********  *****  ****  *    **  **    *  ***  ****    ****

HDUB7  GCACCTGGAGCAGAGAGGGGCCCTCCCGAGGACCGCGACGCCGAGCCTCAGCCTGGCAGC  2262
MDUB7  TGGACTACGACAGGGGGAAGCTCTCCAAAGGACCCTGTTTCACAGCTGGAGCCCATCAGT  2247
       **    ***  ***  *  **  ****  ******    *    *    ***    ****      ***

HDUB7  CCCGCCGCCGAATCCCTGGAGGAGCCAGATGCGGCCGCCGGCCTCAGCA---GCACCAAG  2319
MDUB7  GATGAGCCCAGTCCCCTTGAGATACCGGAGGCTGTCACCAATGGGAGCACACAGACCCCT  2307
       *      **    ****  ***    **  **  **  *  *  **      ****      ***

HDUB7  AAGGCTCCGCCGCCCCGCGATCCCGGCACCCCCGCTACCAAAGAAGGCGCCTGGGAGGCC  2379
MDUB7  TCCACCACATCACCCCTGGAGCCCACCATCAGCTGTACCAAAGAAGACTCGTCCGTTGTT  2367
       *    *    *  ****    **  ***    **  *    *  **********  *    *    *    *

HDUB7  ATGGCCGTCGCCCCCGAGGAG-------CCTCCGCCC-----------AGCGCCGGCGAG  2421
MDUB7  GTCTCAGCTGAACCTGTGGAGGGTTTGCCTTCCGTCCCTGCTCTTTGTAACAGCACTGGT  2427
       *    *    *    **  ****        *  ****  **                *    *    *    *

HDUB7  GACATCGTGGGGACACAGCACCCCCTGACCTGTGTGATCCCGGGAGCTTAACAGGCGAT  2481
MDUB7  ACTATCTTGGGGGATACCCCAGTGCCCGAATTGTGTGACCCTGGAGACTTGACTGCCAAC  2487
       ***  *******  **  **      **  **  *******  **  **      ***  **  *  *  *

HDUB7  GCGAGCCCGTTGTCCCAGGACGCAAAGGGGATGATCGCGGAGGGCCCGCGGGACTCGGCG  2541
MDUB7  CCGAGCCAGCCAACCGAAGCAGTGAAAGGTGATACAGCTGAGAAGGCTCAGGACTCTGCC  2547
       ******  *    **  *  *    **  **      *  **  ***      *  *  ******  **

HDUB7  TTGGCGGAAGCCCCGGAAGGGTTGAGTCCGGCTCCGCCTGCGCGGTCGGAGGAGCCCTGC  2601
MDUB7  ATGGCTGAAGTGGTGGAGAGGCTGAGCCCTGCTCCCTCAGTACTCACAGGTGACGGGTGT  2607
       ****  ****      ***  **  ****  **  *****    *    *      *    **        **

HDUB7  GAGCAGCCACTCCTTGTTCACCCCAGCGGGGACCACGCCCGGGACGCTCAGGACCCATCC  2661
MDUB7  GAGCAGAAACTCTTACTTTACCTCAGCGCAGAGGGTCAGAGGAGACAGAAGACTCTTCC  2667
       ******    ****  *  **  ***  *****  **        *    ***      *    *  ***    ***

HDUB7  CAGAGCTTGGGCGCACCCGAGGCCGCAGAGCGGCCGCCAGCTCCTGTGCTGGACATGGCC  2721
MDUB7  AGAAGCTCGGCGGTCTCTGCTGACACGATGC---------CCCCTAAGCCTGACAGGACC  2718
       ****** **  *    *    *  *  *    **            *  ***  **  ****  *  **

HDUB7  CCGGCCGGTCACCCGGAAGGGGACGCTGAGCCTAGCCCCGGCGAGAGGGTCGA-GGACGC  2780
MDUB7  ACCACCAGCTCCTGTGAAGGGGCTGCCGAGCAGGCTGCTGGGGACAGAGGCGATGGAGGC  2778
       *  **  *      *    *******  **  ****          *  **  **  **  *  ***  ***  **

HDUB7  C--GCGGCGCCGAAAGCCCCAGGCCCTTCCCCAGCGAAGGAGAAAATCGGCAGCCTCAGA  2838
MDUB7  CATGTGGGACCCAAAGCTCAGGAGCCTTCCCCAGCAAGGAAAAAGATGAGCAGCCTCCGG  2838
       *    *  **    **  *****  *    *    ***********  *****    **  **  ********  *

HDUB7  AAGGTGGACCGAGGCCACTACCGCAGCCGGAGAGAGCGCTCGTCCAGCGGGGAGCCCGCC  2898
MDUB7  AAAGTGGACCGAGGACACTATCGGAGCCGGAGAGAGCGCTCCTCCAGTGGGGAGCACGTG  2898
       **  ***********  *****  *  **  *******************  *****  *******  **

HDUB7  AGAGAGAGCAGGAGCAAGACTGAGGGCCACCGTCACCGGCGGCGCCGCACCTGCCCCCGG  2958
MDUB7  AGGGACAGCAGGCCCCGGCCGGAGGACCATCACCATAAGAAGCGGCACTGCTACAGCCGA  2958
       **  **  ******    *  *  ****  ***  *  **    *  ***  *  **  *  ***

HDUB7  GAGCGCGACCGCCAGGACCGCCACGCCCC------------------GGAGCACCACCCC  3000
MDUB7  GAGCGGCCCAAGCAGGACCGACACCCTACTAATTCATACTGCAATGGGGGCCAGCACTTG  3018
       *****    *  ********  ***  *    *                          **  **  ***

HDUB7  GGCCACGGCGACAGGCTCAGCCCTGGCGAGCGCCGCTCTCTGGGCAGGTGCAGTCACCAC  3060
MDUB7  GGCCACGGGACAGAGCCAGCCCT---GAGCGCCGCTCCCTGAGCAGGTATAGTCACCAC  3075
       ********  *****      *******    ***********  ***  ******    *********

HDUB7  CACTCCCGACACCGGAGCGGGGTGGAGCTGGACTGGGTCAGACACCACTACACCGAGGGC  3120
MDUB7  CACTCACGGATTAGGAGTGGCCTGGAGCAGGACTGGAGCCGGTACCACATTTGGAAAAT  3135
       *****  **    ****  **  ******  *******    *  *  *****  *      **
```

TABLE 15-continued

Nucleotide sequence alignment of hDUB7 SEQ ID No.8)
and mDUB7 SEQ ID No.11)

```
HDUB7  GAGCGTGGCTGGGGCCGGGAGAAGTTCTACCCCGACAGGCCGCGCTGGGACAGGTGCCGG  3180
MDUB7  GAGCATGCTTGGGTCAGGGAGAGATTCTACCAGGACAAGCTGCGGTGGGACAAGTGCAGG  3195
       **** **  **** * ******  ******* **** ** *** ******* **** **

HDUB7  TACTACCATGACAGGTACGC---CCTGTACGCTGCCCGGGACT----GGAAGCCCTTCCA  3233
MDUB7  TATTACCACGACAGGTACACGCCCCTATACACGGCCCGGGACGCCCGAGAATGGCGGCCT  3255
       ** ***** ********* *   *** *** * *********      ***  *  **

HDUB7  CGGC--GGCCGCGAGCACGAGCGGGCCGGGCTGCACGAGCGGCCGCACAAGGACCACAAC  3291
MDUB7  CTGCATGGTCGTGAGCATGACCGCCTTGTCCAGTCTGGACGGCCATACAAGGACAGCTAC  3315
       * **  **  ** ***** **  **       *   *  * *****  ******** **

HDUB7  CGGGGCCGTAGGGGCTGCGAGCCGG---CCCGGGAGAGGGAGCGGCACCGCCCCAGCAGC  3348
MDUB7  TGGGGCCGCAAGGGCTGGGAGCTGCAATCCCGGGGGAAGGAACGGCCCCACTTCAACAGC  3375
       *******  * ****** *****  *    ****** ** *** ****  **  * ****

HDUB7  CCCCGCAGGCGCGCCCCACGCCCTCGCCCCGCACCCCGACCGCTTCTCCCACGACAGA   3408
MDUB7  CCCCGAGAGG------CCCCTAGCCTTGCTGTGCCCCTCGAGAGACATCTCCAAGAGAAG  3429
       ***** * **      *** *** **  ** ** ***  *    *** ** *

HDUB7  ACTGCACT---TGTAGCCGGAGACAACTGTAACCTCTCTGATCGGTTTCACGAACACGAA  3465
MDUB7  GCTGCGCTGAGTGTGCAGGACAGCAGCCACAGTCTCCCTGAGCGCTTTCATGAACACAAA  3489
       **** **   *** *    **  **   *  *** **** ** ***** ****** **

HDUB7  AATGGAAAGTCCCGGAAACGGAGACACGACAGTGTGGAGAACAGTGACAGTCATGTTGAA  3525
MDUB7  AGTGTCAAGTCGAGGAAGCGGAGGTATGAGACTCTAGAAAATAATGATGGCCGTCTAGAA  3549
       * **  *****   ****  ****    ** * *  ** ** * ** **   **  ***

HDUB7  AAGAAAGCCCGGAGGAGCGAACAGAAGGATCCTCTAGAAGAGCCTAAAGCAAAGAAGCAC  3585
MDUB7  AAGAAAGTCCACAAAAGCCTGGAGAAGGACACGCTAGAGGAGCCAAGGGTGAAGAAGCAC  3609
       ******* **  *  ***    ******  * ***** ***** *    ********

HDUB7  AAAAAATCAAAGAAGAAAAAGAAATCCAAAGACAAACACCGAGACCGCGACTCCAGGCAT  3645
MDUB7  AAAAAGTCTAAAAAGAAAAAGAAGTCCAAAGATAAACACCGGGATCGAGAAAGCAGGCAC  3669
       ***** ** ** *********** ******* ******** ** ** **    *****

HDUB7  CAGCAGGACTCAGACCTCTCAGCAGCGTGCTCTGACGCTGACCTCCACAGACACAAAAAA  3705
MDUB7  CAGCAGGAGTCTGATTTTTCAGGAGCATACTCTGATGCTGACCTCCATAGACACCGGAAG  3729
       ******** ** **  * **** *** * ***** ***********  *****   **

HDUB7  AAGAAGAAGAAAAAGAAGAGACATTCAAGAAAATCAGAGGACTTTGTTAAAGATTCAGAA  3765
MDUB7  AAAAAGAAGAAAAAGAAAAGGCATTCCAGGAAGTCGGAGGACTTTATAAAGGATGTTGAG  3789
       ** ************** ** ***** ** ** ** ********   *** *** * *

HDUB7  CTGCACTTACCCAGGGTCACCAGCTTGGAGACTGTCGCCCAGTTCCGGAGAGCCCAGGGT  3825
MDUB7  ATGCGTTTACCGAAGCTCTCCAGCTACGAGGCCGGCGGCCATTTCCGGAGAACAGAGGGC  3849
       ***  ***** *  * ** ****** *** **  ** ** ********* *  ****

HDUB7  GGCTTTCCTCTCTCTGGTGGCCCGCCTCTGGAAGGCGTCGGACCTTTCCGTGAGAAAACG  3885
MDUB7  AGCTTTCTCCTGGCTGATGGTCTGCCTGTGGAAGACAGCGGCCCTTTCCGGGAGAAAACG  3909
        ******  ***  **  ** ****** ******  *  ***  ******* ********

HDUB7  AAACACTTACGGATGGAAAGCAGGGATGACAGGTGTCGTCTCTTTGAGTATGGCCAGGGT  3945
MDUB7  AAGCATTTAAGGATGGAAAGCCGGCCTGACAGATGCCGTCTGTCGGAGTATGGCCAGGAT  3969
       ** ** *** *********** **  ***** ** ***** *  *************

HDUB7  GATTGA------  3951
MDUB7  TCAACATTTTGA  3981
```

TABLE 16

Deduced amino acid sequence alignment of hDUB7 and MDUB7

```
HDUB7  MTIVDKASESSDPSAYQNQPGSSEAVSPGDMDAGSASWGAVSSLNDVSNHTLSLGPVPGA  60
MDUB7  MTIVDKT-EPSDPSTCQNQPGSCEAVSPEDMDTGSASWGAVSSISDVSSHTLPLGPVPGA  59
       ******: *.****: ****** ****** ***:*********:.***.***.*******

HDUB7  VVYSSSSVPDKSKPSPQKDQALGDGIAPPQKVLFPSEKICLKWQQTHRVGAGLQNLGNTC  120
MDUB7  VVYSNSSVPEKSKPSPPKDQVLGDGIAPPQKVLFPSEKICLKWQQSHRVGAGLQNLGNTC  119
       ****.***** ***** ***.***********************:**************
```

TABLE 16-continued

Deduced amino acid sequence alignment of hDUB7 and MDUB7

```
HDUB7  FANAALQCLTYTPPLANYMLSHEHSKTCHAEGFCMMCTMQAHITQALSNPGDVIKPMFVI  180
MDUB7  FANAALQCLTYTPPLANYMLSHEHSKTCHAEGFCMMCTMQTHITQALSNPGDVIKPMFVI  179
       ***************************************:********************

HDUB7  NEMRRIARHFRFGNQEDAHEFLQYTVDAMQKACLNGSNKLDRHTQATTLVCQIFGGYLRS  240
MDUB7  NEMRRIARHFRFGNQEDAHEFLQYTVDAMQKACLNGSNKLDRHTQATTLVCQIFGGYLRS  239
       ************************************************************

HDUB7  RVKCLNCKGVSDTFDPYLDITLEIKAAQSVNKALEQFVKPEQLDGENSYKCSKCKKMVPA  300
MDUB7  RVKCLNCKGVSDTFDPYLDITLEIKAAQSVTKALEQFVKPEQLDGENSYKCSKCKKMVPA  299
       ******************************.*****************************

HDUB7  SKRFTIHRSSNVLTLSLKRFANFTGGKIAKDVKYPEYLDIRPYMSQPNGEPIVYVLYAVL  360
MDUB7  SKRFTIHRSSNVLTISLKRFANFTGGKIAKDVKYPEYLDIRPYMSQPNGEPIIYVLYAVL  359
       **************:*************************************:*******

HDUB7  VHTGFNCHAGHYFCYIKASNGLWYQMNDSIVSTSDIRSVLSQQAYVLFYIRSHDVKNGGE  420
MDUB7  VHTGFNCHAGHYFCYIKASNGLWYQMNDSIVSTSDIRAVLNQQAYVLFYIRSHDVKNGGE  419
       *************************************:**.*******************

HDUB7  LTHPTHSPGQSSPRPVISQRVVTNKQAAPGFIGPQLPSHMIKWPPHLNGTGPLKDTPSSS  480
MDUB7  SAHPAHSPGQSSPRPGVSQRVVNNKQVAPGFIGPQLPSHVMKNTPHLNGTTPVKDTPSSS  479
       :***********.****:***..***:************:**.******.*:*******

HDUB7  MSSPNGNSSVNRASPVNASASVQNWSVNRSSVIPEHPKKQKITISIHNKLPVRQCQSQPN  540
MDUB7  VSSPNGNTSVNRASPATASTSVQNWSVTRPSVIPDHPKKQKITISIHNKLPARQGQAPLN  539
       :******.*******..**:*******.*.****:***************.**  *:  *

HDUB7  --LHSNSLENPTKPVPSSTITN-SAVQSTSNASTMSVSSKVTKPIPRSESCSQPVMNGKS  597
MDUB7  NSLHGPCLEAPSKAAPSSTITNPSAIQSTSNVPTTSTS--------PSEACPKPMVNGKA  591
       **.  .** .**..******* ** .***** .* *.*         *:.:*:****:

HDUB7  KLNSSVLVPYGAESSEDSDEESKGLGKENGIGTIVSSHS--PGQDAED-EEATPHELQEP  654
MDUB7  KVGASVLVPYGAESSEESDEESKGLAKENGVDMMAGTHSDRPEAAADDGAEASSHELQEP  651
       *:..:***********:********.****:. :..:** *:* **:.******

HDUB7  MTLNGANSADSDSDPKENGLAPDGASCQGQPALHSENPFAKANGLPGKLMPAPLLSLPED  714
MDUB7  VLLNGANSADSDS--QENSLAFDSASCQVPELHTENLFSKLNGLPGKVTPAPLQSVPED  709
       : ***********  :**.**.****  *  **:** *:****** : ****  *.***

HDUB7  KILETFRLSNKLKGSTDEMSAPGAERGPPEDRDAEPQPGSPAAESLEEPDAAA-GLSSTK  773
MDUB7  RILETFKLTNQAKGPAGEESWTTTGGSSPKDPVSQLEPISDEPSPLEIPEAVTNGSTQTP  769
       :*****:*:*:  **. . * . :  ..*:*  ::  :*  *   ...** *:*.: * :.*

HDUB7  KAPPPRDPGTPATKEGAWEAMAVAPEEPPP------SAGEDIVGDTAPPDLCDPGSLTGD  827
MDUB7  STTSPLEPTISCTKEDSSVVVSAEPVEGLPSVPALCNSTGTILGDTPVPELCDPGDLTAN  829
       .:...* :*   ..***.:  .::. * *  *       .: *:***. *:*****.**.:

HDUB7  ASPLSQDAKGMIAEGPRDSALAEAPEGLSPAPPARSEEPCEQPLLVHPSGDHARDAQDPS  887
MDUB7  PSQPTEAVKGDTAEKAQDSAMAEVVERLSPAPSVLTGDGCEQKLLLYLSAEGSEETEDSS  889
       .*  ::  **   **  .:***:**.  *****..  :  : *** **::  *..:::*.*

HDUB7  QSLGAPEAAERPPAPVLDMAPAGHPEGDAEPSPGERVED-AAAPKAPGPSPAKEKIGSLR  946
MDUB7  RSS-AVSADTMPPKP--DRTTTSSCEGAAAEQAAGDRGDGGHVGPKAQEPSPAKEKMSSLR  946
       :*  * .*    ** * *   :.:  ** **   :.*:* :.   ..*** *******:.***

HDUB7  KVDRGHYRSRRERSSSGEPARESRSKTEGHRHRRRRTCPRERDRQDRHAP------EHHP  1000
MDUB7  KVDRGHYRSRRERSSSGEHVRDSRPRPEDHHHKKRHCYSRERPKQDRHPTNSYCNGGQHL  1006
       ****************** .*:**.:.*.*:*::*:*: .*** :****..       :*

HDUB7  GHGDRLSPGERRSLGRCSHHHSRHRSGVELDWVRHHYTEGERGWGREKFYPDRPRWDRCR  1060
MDUB7  GHGDRASP-ERRSLSRYSHHHSRIRSGLEQDWSRYHHLENEHAWVRERFYQDKLRWDKCR  1065
       ***** **.****.* ****** ***.* **.*:*: *.:*.* ****:*: ***:**

HDUB7  YYHDRYA-LYAAR---DWKPFHGGREHERAGLHERPHKDHNRGRRGCEP-ARERERHRPS  1115
MDUB7  YYHDRYTPLYTARDAREWRPLHG-REHDRLVQSGRPYKDSYWGRKGWELQSRGKERPHFN  1124
       ******:  **:**    :*:** ****. *   **::***.  **:* *  ****:*  .

HDUB7  SPRAGAPHALAPHPDRFSHDRTALVAGDNCN-LSDRFHEHENGKSRKRRHDSVENSDSHV  1174
MDUB7  SPREAP--SLAVPLERHLQEKAALSVQDSSHSLPERFHEHKSVKSRKRRYETLENNDGRL  1182
       ***  .. :**.  :*:  .:::**  . *...: *.******:. ******:::**.*.::

HDUB7  EKKARRSEQKDPLEEPKAKKHKKSKKKKKSKDKHRDRDSRHQQDSDLSAACSDADLHRHK  1234
MDUB7  EKKVHKSLEKDTLEEPRVKKHKKSKKKKKSKDKHRDRESRHQQESDFSGAYSDADLHRHR  1242
       ***.::* *:**.****:.************** *****:****:**:*.* ********:
```

TABLE 16-continued

Deduced amino acid sequence alignment of hDUB7 and MDUB7

```
HDUB7  KKKKKKKRHSRKSEDFVKDSELHLPRVTSLETVAQFRRAQGGFPLSGGPPLEGVGPFREK  1294
MDUB7  KKKKKKKRHSRKSEDFIKDVEMRLPKLSSYEAGGHFRRTEGSFLLADGLPVEDSGPFREK  1302
       *************** ** *:**:::* *: .:***::*.* *:.* *:*. ******

HDUB7  TKHLRMESRDDRCRLFEYGQGD--  1316
MDUB7  TKHLRMESRPDRCRLSEYGQDSTF  1326
       ********* ***** ****..
```

TABLE 16

Amino acid sequence alignment of catalytic domain among murine DUB1, DUB2, hDUB7 and mDUB7. Amino acids that are involved in catalysis in DUB1 (Cys-60, Asp-133, and His-307) are underlined.

```
mDUB1  MVVALSFPEADPALSSPDAPELHQDEAQVVEELTVNGKHSLSWESPQGPGCGLQNTGNSC  60
mDUB2  MVVSLSFPEADPALSSPGAQQLHQDEAQVVVELTANDKPSLSWECPQGPGCGLQNTGNSC  60
hDUB7  VVYSSSSVPDKSKPSPQKDQALGDGIAPPQKVLFPSEKICLKWQQTHRVGAGLQNLGNTC  120
mDUB7  VVYSMSSVPEKSKPSPPKDQVLGDGIAPPQKVLFPSEKICLKWQQSHRVGAGLQMLGNTC  119
       :* : *   .. *.   * :. *      * . * .*.*: .: *.** :* mDUB1  YLNAALQCLTHTPPLADYMLSQEHSQTCCSPEGCKLCAMEALVTQSLLHSHSGDVMKPSH  120
mDUB2  YLNAALQCLTHTPPLADYMLSQEYSQTCCSPEGCKMCAMEAHVTQSLLHSHSGDVMKPSQ  120
hDUB7  FANAALQCLTYTPPLANYMLSHEHSKTCHAEGFCMMCTMQAHITQALSN--PGDVIKPMF  178
mDUB7  FANAALQCLTYTPPLANYMLSHEHSKTCHAEGFCMMCTMQTHITQALSN--PGDVIKPMF  177
       : ********:*****:****:*:**:** :    * :*:*:: :**:* :  .***:**

mDUB1  ILTSA------FHKHQQEDAHEFLMFTLETMHESCLQVHRQSKPTSEDSSPIHDIFGGWW  174
mDUB2  ILTSA------FHKHQQEDAHEFLMFTLETMHESCLQVHRQSEPTSEDSSPIHDIFGGLW  174
hDUB7  VINEMRRIARHFRFGNQEDAHEFLQYTVDANQKACLNGSNKLDRHTQATTLVCQIFGGYL  238
mDUB7  VINEMRRIARHFRFGNQEDAHEFLQYTVDANQKACLNGSNKLDRHTQATTLVCQIFGGYL  237
       ::..       *: :******** :*:::*:**:  .: .  :: :: :*:**** mDUB1  RSQIKCLLCQGTSDTYDRFLDIPLDISSAQSVKQALWDTEKSEELCGDNAYYCGKCRQKM  234
mDUB2  RSQIKCLHCQGTSDTYDRFLDVPLDISSAQSVNQALWDTEKSEELRGENAYYCGRCRQKM  234
hDUB7  RSRVKCLNCKGVSDTFDPYLDITLEIKAAQSVNKALEQFVKPEQLDGENSYKCSKCKKMV  298
mDUB7  RSRVKCLNCKGVSDTFDPYLDITLEIKAAQSVTKALEQFVKPEQLDGENSYKCSKCKKMV  297
       **::*** *:*.****:* :**:  :.*.:****.***  :  *.:*  *:*:* :

mDUB1  PASKTLHVHIAPKVLMVVLNRFSAFTGNKLDRKVSYPEFLDLKPYLSEPTGGPLPYALYA  294
mDUB2  PASKTLHIHSAPKVLLLVLKRFSAFMGNKLDRKVSYPEFLDLKPYLSQPTGGPLPYALYA  294
hDUB7  PASKRFTIHRSSNVLTLSLKRFANFTGGKIAKDVKYPEYLDIRPYMSQPNGEPIVYVLYA  358
mDUB7  PASKRFTIHRSSNVLTISLKRFANFTGGKIAKDVKYPEYLDIRPYMSQPNGEPIIYVLYA  357
       **** : :* .: : :  * .*: :..*:.*:::**:*:*.*.*:  *:*** mDUB1  VLVHDGATSHSGHYFCCVKAGHGKWYKMDDTKVTRCDVTSVLNENAYVLFYVQQANLKQ  352
mDUB2  VLVHEGATCHSGHYFSYVKARHGAWYKMDDTKVTSCDVTSVLNENAYVLFYVQQTDLKQ  352
hDUB7  VLVHTGFNCHAGHYFCYIKASNGLWYQMNDSIVSTSDIRSVLSQQAYVLFYIRSHDVKN  417
mDUB7  VLVHTGFNCHAGHYFCYIKASNGLWYQMNDSIVSTSDIRAVLNQQAYVLFYIRSHDVKN  416
       **** * ..*:****. :** :* **:*:* *: .*: :**.::*******:: .::*:
```

What is claimed is:

1. An isolated polypeptide comprising SEQ ID NO: 9.

* * * * *